(12) United States Patent
Kowalski et al.

(10) Patent No.: US 8,071,638 B2
(45) Date of Patent: Dec. 6, 2011

(54) SOLID STATES OF ATORVASTATIN POTASSIUM

(75) Inventors: Yoav Kowalski, Ramat Gan (IL); Ariel Mittelman, Elad (IL); Sigalit Levi, Modi'in (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 202 days.

(21) Appl. No.: 12/536,682

(22) Filed: Aug. 6, 2009

(65) Prior Publication Data
US 2010/0041731 A1 Feb. 18, 2010

Related U.S. Application Data

(60) Provisional application No. 61/189,155, filed on Aug. 14, 2008, provisional application No. 61/190,393, filed on Aug. 27, 2008, provisional application No. 61/197,492, filed on Oct. 27, 2008, provisional application No. 61/199,809, filed on Nov. 19, 2008, provisional application No. 61/214,858, filed on Apr. 28, 2009, provisional application No. 61/268,771, filed on Jun. 15, 2009.

(51) Int. Cl.
*A61K 31/40* (2006.01)
*C07D 207/34* (2006.01)
(52) U.S. Cl. ........................................ 514/423; 548/537
(58) Field of Classification Search .................. 548/537; 514/423
See application file for complete search history.

(56) References Cited

U.S. PATENT DOCUMENTS
4,681,893 A 7/1987 Roth
5,273,995 A 12/1993 Roth

FOREIGN PATENT DOCUMENTS
WO WO 2006/021216 3/2006

OTHER PUBLICATIONS
U.S. Appl. No. 60/166,153, filed Nov. 17, 1999, Ayalon et al.

*Primary Examiner* — Jason M Nolan
(74) *Attorney, Agent, or Firm* — Kenyon & Kenyon LLP

(57) ABSTRACT

Atorvastatin potassium crystalline Forms A, B, E, F, and G are provided. Also provided are methods of preparing atorvastatin potassium crystalline Forms A, B, E, F, and G. Atorvastatin potassium crystalline Forms A, B, E, F, and G may be used to prepare pharmaceutical compositions useful for the treatment of hypercholesterolemia or hyperlipidemia.

19 Claims, 21 Drawing Sheets

SOLID STATES OF ATORVASTATIN POTASSIUM

CROSS REFERENCE TO RELATED APPLICATIONS

This application claims the benefit of U.S. Provisional Patent Application Ser. No. 61/189,155, filed Aug. 14, 2008, U.S. Provisional Patent Application Ser. No. 61/190,393, filed Aug. 27, 2008, U.S. Provisional Patent Application Ser. No. 61/197,492, filed Oct. 27, 2008, U.S. Provisional Patent Application Ser. No. 61/199,809, filed Nov. 19, 2008, U.S. Provisional Patent Application Ser. No. 61/214,858, filed Apr. 28, 2009, and U.S. Provisional Patent Application Ser. No. 61/268,771, filed Jun. 15, 2009, the contents of which are incorporated by reference herein, in their entireties.

FIELD OF THE INVENTION

The present invention relates to solid forms of atorvastatin potassium and novel processes for preparing said solid forms of atorvastatin potassium.

BACKGROUND OF THE INVENTION

Atorvastatin, ([R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid), depicted in lactone form in Formula (I) and its calcium salt trihydrate of Formula (II) (water molecules not shown) are well known in the art, and described, inter alia, in U.S. Pat. Nos. 4,681,893 and 5,273,995, and in U.S. Provisional Patent Application No. 60/166,153, filed Nov. 17, 2000, all of which are herein incorporated by reference.

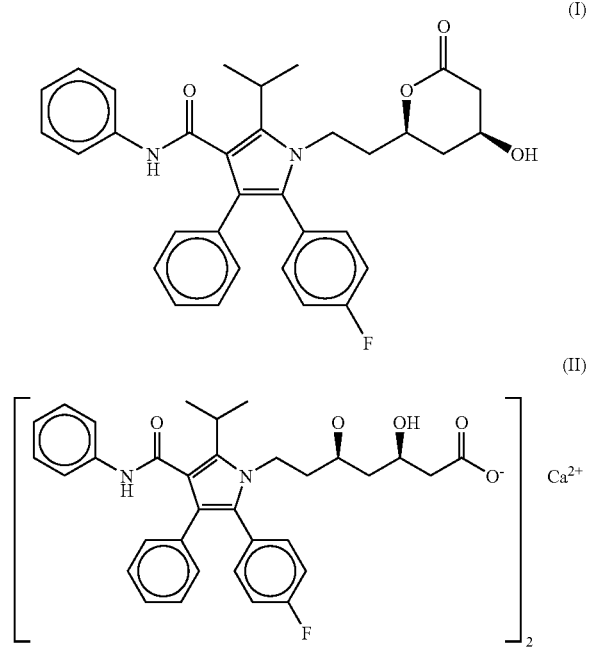

Three polymorphs of the potassium salt of atorvastatin, namely I, II and III are disclosed in International Patent Publication WO 06/021216, and characterized by X-ray powder diffraction. Form II was described as an amorphous material, while forms I and III were characterized by the following XRPD peaks in degrees 2θ:

| Form I | Form III |
|---|---|
| 8.4 | 7.64 |
| 9.0 | 9.26 |
| 10.0 | 9.76 |
| 10.5 | 10.14 |
| 11.24 | 14.1 |
| 16.38 | 16.5 |
| 17.46 | 17.1 |
| 18.12 | 18.44 |
| 19.92 | 19.74 |
| 20.98 | 20.32 |
| 22.08 | 20.82 |
| 23.24 | 21.32 |
| 23.84 | 22.98 |
| 25.2 | 24.34 |
| 27.8 | 25.82 |
| 29.6 | 27.34 |
| 31.3 | 28.84 |
| 32.16 | 30.56 |
| 36.34 | 37.32 |
| 42.8 | 39.2 |

Form I was also characterized by a melting peak of 155-165° C. in its DSC. Form II was characterized by a melting peak at 173-183° C. and form III was characterized by a melting peak at 143-156° C. in the DSC.

SUMMARY OF THE INVENTION

The present invention provides a solid crystalline atorvastatin potassium, denominated as Form A, characterized by data selected from the group consisting of: an X-ray powder diffraction (XRPD) pattern having peaks at about 2.7 and 8.0±0.3 degrees 2θ and a broad peak with maximum at about 18.5±0.3 degrees 2θ, a solid-state $^{13}$C NMR spectrum with signals at about 126.5, 133.0 and 167.5±0.2 ppm, a solid-state $^{13}$C NMR spectrum having chemical shift differences between the signal exhibiting the lowest chemical shift and another signal in the chemical shift range of 100 to 200 ppm of about 10.9, 17.4 and 51.9±0.1 ppm wherein the lowest chemical shift in the chemical shift area of 100 to 200 ppm is at about 115.6±1 ppm, and combinations thereof.

Another aspect of the present invention is a process for preparing atorvastatin potassium Form A. The method of preparing atorvastatin potassium Form A comprises providing a mixture of atorvastatin, THF or an ethanol:water mixture, and potassium hydroxide, and precipitating atorvastatin potassium Form A out of the reaction mixture by removing the solvent or by combining the mixture with an antisolvent that is a liquid $C_4$-$C_6$ ether or a $C_5$-$C_{10}$ alkane.

Yet another aspect of the present invention is a process for preparing atorvastatin potassium Form A. The method of preparing atorvastatin potassium Form A comprises providing a mixture of atorvastatin, THF or 2-methyl THF, water and potassium hydroxide, and precipitating atorvastatin potassium Form A out of the reaction mixture by evaporation.

The present invention further encompasses a crystalline form of atorvastatin potassium, denominated as Form B, characterized by data selected from the group consisting of: an X-ray powder diffraction (XRPD) pattern having peaks at about 8.8, 19.0 and 20.5±0.3 degrees 2θ, and at least two peaks selected from the group consisting of 7.7, 9.8, 21.6, 23.9 and 26.9±0.3 degrees 2θ, an XRPD pattern having peaks at about 8.8, 19.0, 20.5, 23.9, and 26.9±0.3 degrees 2θ, a solid-state $^{13}$C NMR spectrum with signals at about 129.2, 166.2 and 177.2±0.2 ppm, a solid-state $^{13}$C NMR spectrum having chemical shift differences between the signal exhibiting the lowest chemical shift and another signal in the chemical shift range of 100 to 200 ppm of about 11.6, 48.6 and 59.6±0.1 ppm wherein the lowest chemical shift in the chemical shift area of 100 to 200 ppm is at about 117.6±1 ppm, and combinations thereof.

Another aspect of the present invention is a process for preparing atorvastatin potassium Form B. The method of preparing atorvastatin potassium Form B comprises providing a mixture of atorvastatin, ethanol and potassium hydroxide, and precipitating atorvastatin potassium Form B out of the reaction mixture by combining the reaction mixture with an antisolvent that is a $C_6$-$C_{10}$ aromatic hydrocarbon.

A further aspect of the present invention is a process for preparing atorvastatin potassium Form III comprising suspending atorvastatin potassium Form A in ethanol.

The present invention further encompasses a crystalline form of atorvastatin potassium, denominated as Form E, characterized by an X-ray powder diffraction (XRPD) pattern having peaks at about 4.5, 6.5-8.3 (broad peak) and 9.2±0.3 degrees 2θ as depicted in FIG. 19.

Another aspect of the present invention is a process for preparing atorvastatin potassium Form E. The method of preparing atorvastatin potassium Form E comprises grinding atorvastatin potassium Form A in the presence of water.

The present invention further encompasses a crystalline form of atorvastatin potassium, denominated as Form F, characterized by an X-ray powder diffraction (XRPD) pattern having peaks at about 4.5, 5.1, 7.6, 11.2 and 17.6±0.2 degrees 2θ as depicted in FIG. 20.

Another aspect of the present invention is a process for preparing atorvastatin potassium Form F. The method of preparing atorvastatin potassium Form F comprises grinding atorvastatin potassium Form A in the presence of ethanol.

Another aspect of the present invention is a process for preparing amorphous atorvastatin potassium. The method of preparing amorphous atorvastatin potassium comprises grinding atorvastatin potassium Form I in the presence of water.

The present invention also provides a method for preparing amorphous atorvastatin potassium comprising exposing atorvastatin potassium Form I to about 100% relative humidity.

The present invention further encompasses a crystalline form of atorvastatin potassium, denominated as Form G, characterized by an X-ray powder diffraction (XRPD) pattern having two broad peaks with maxima at about 7.1-7.4 and at about 18.4-20.4±0.2 degrees 2θ, as depicted in FIG. 21.

Another aspect of the present invention is a process for preparing atorvastatin potassium Form G. The method of preparing atorvastatin potassium Form G comprises grinding amorphous atorvastatin potassium in the presence of water.

The present invention further encompasses a process for preparing atorvastatin potassium Form G comprising exposing amorphous atorvastatin potassium to 100% relative humidity.

The present invention encompasses 1) a pharmaceutical composition comprising the atorvastatin potassium crystalline Forms A, B, E, F or G of the present invention and at least one pharmaceutically acceptable excipient, and 2) the use of the crystalline Forms A, B, E, F or G of the present invention, for the manufacture of a pharmaceutical composition, wherein the pharmaceutical composition is useful for the treatment of hypercholesterolemia or hyperlipidemia.

The present invention further encompasses a process for preparing a pharmaceutical composition comprising the atorvastatin potassium crystalline Forms A, B, E, F or G of the present invention, comprising combining the atorvastatin potassium crystalline Forms A, B, E, F or G with at least one pharmaceutically acceptable excipient.

DETAILED DESCRIPTION OF THE INVENTION

Figure 1:
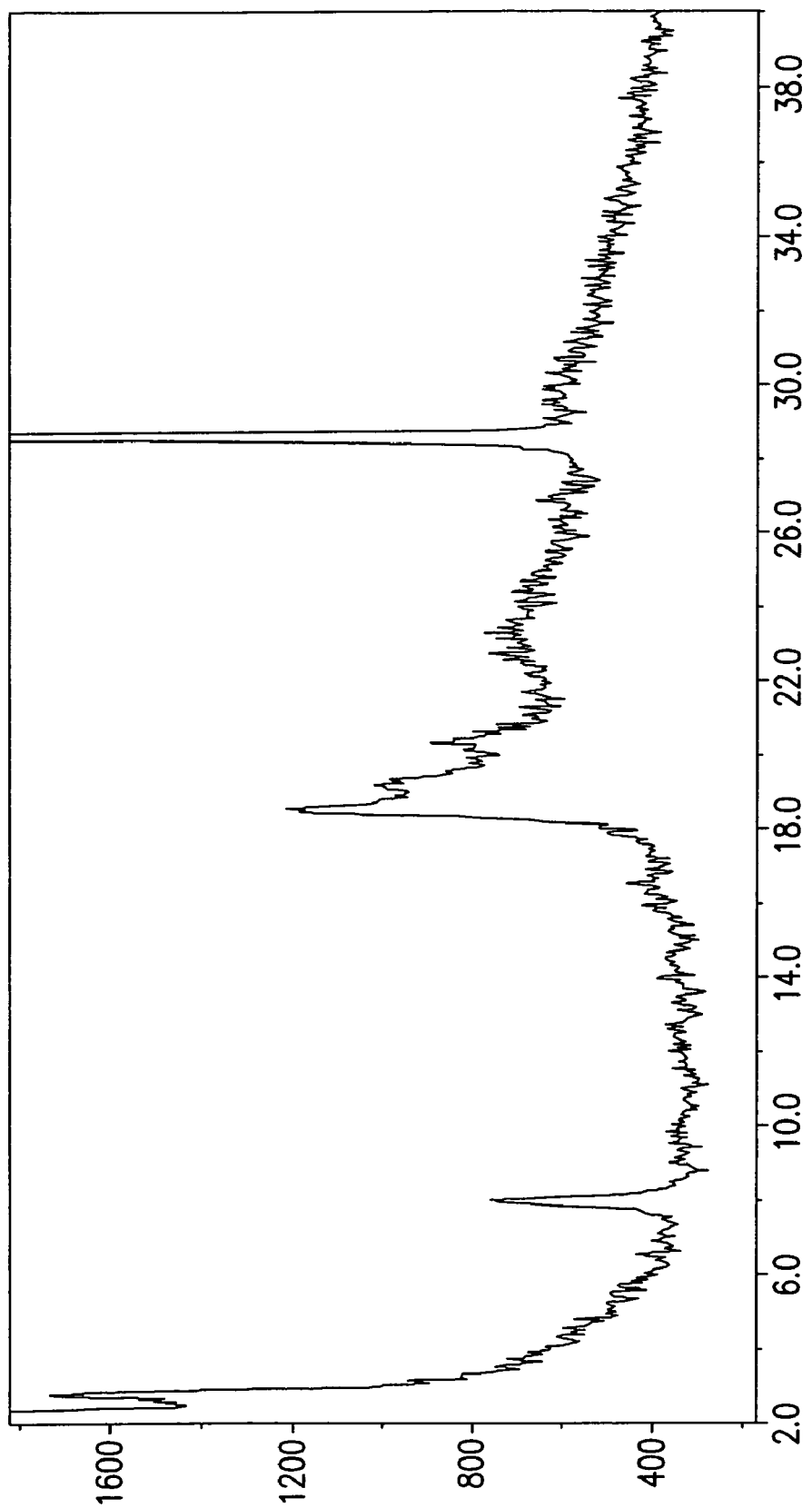
FIG. 1 is a characteristic powder X-ray diffraction pattern (XRPD) of atorvastatin potassium Form A (as prepared in Example 1). The peak at 28.5° is attributed to KCl.
Figure 2:
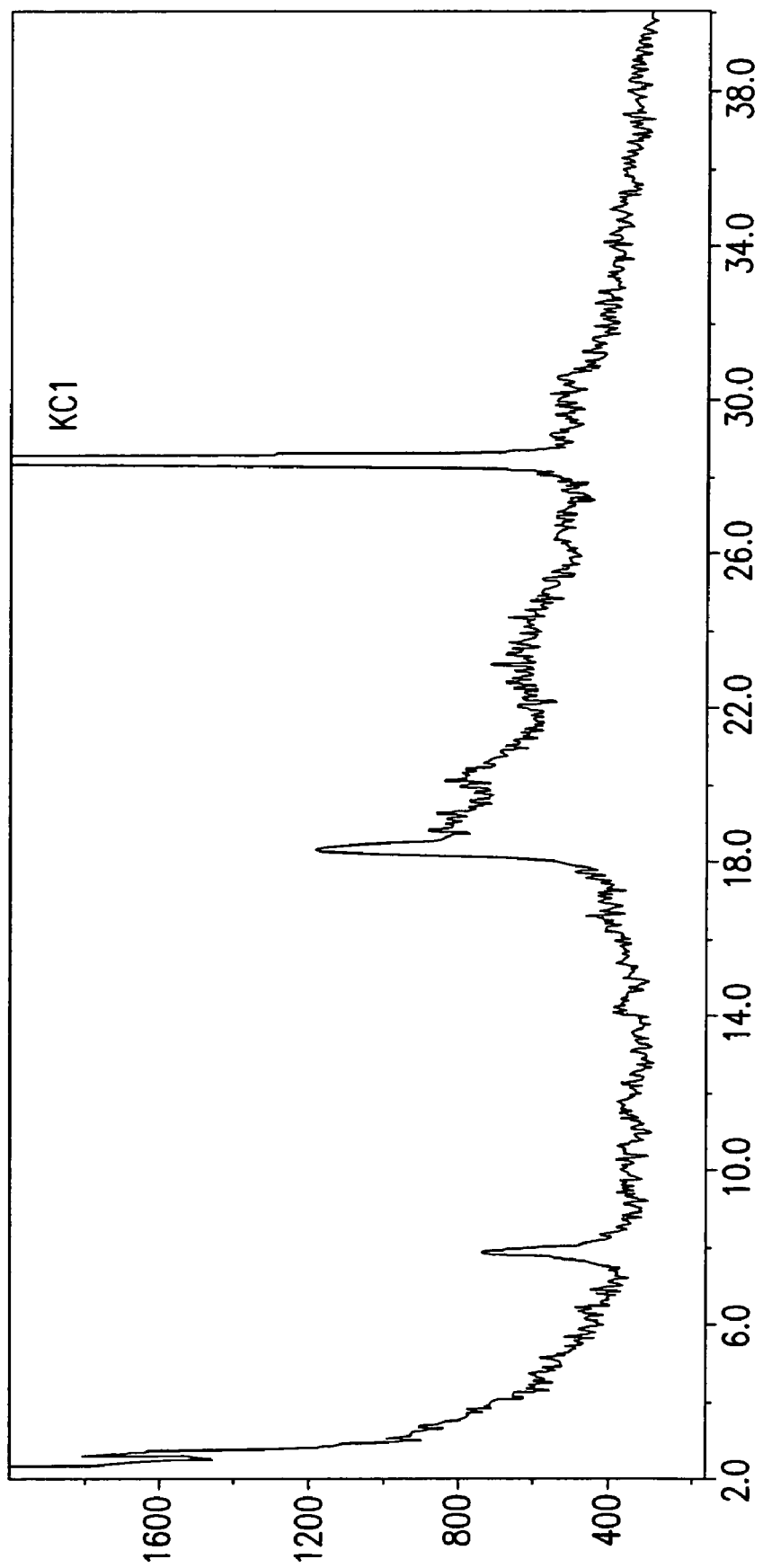
FIG. 2 is a characteristic powder X-ray diffraction pattern (XRPD) of atorvastatin potassium Form A (as prepared in Example 3). The peak at 28.5° is attributed to KCl.
Figure 3:
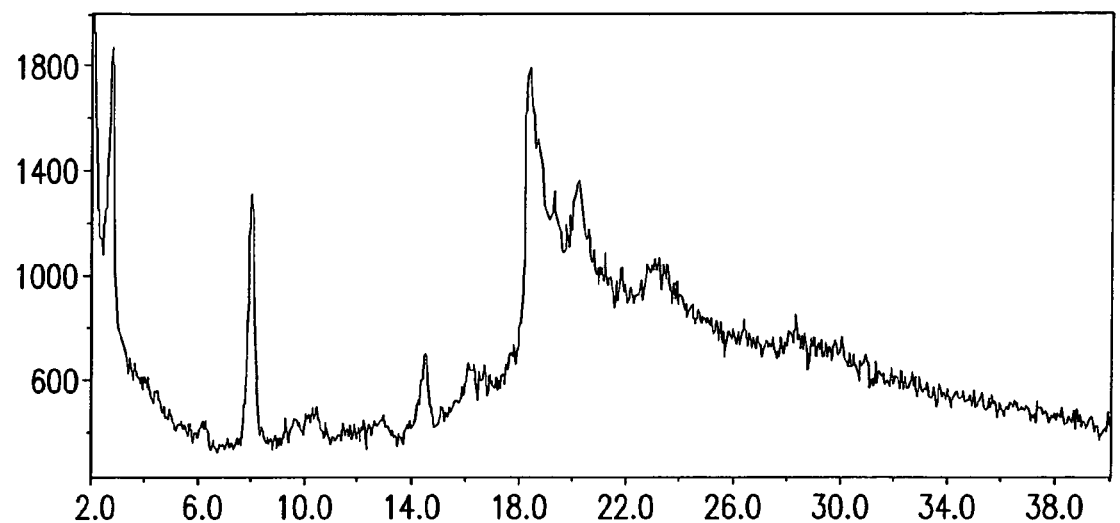
FIG. 3 is a characteristic powder X-ray diffraction pattern (XRPD) of atorvastatin potassium Form A (as prepared in Example 8).
Figure 4:
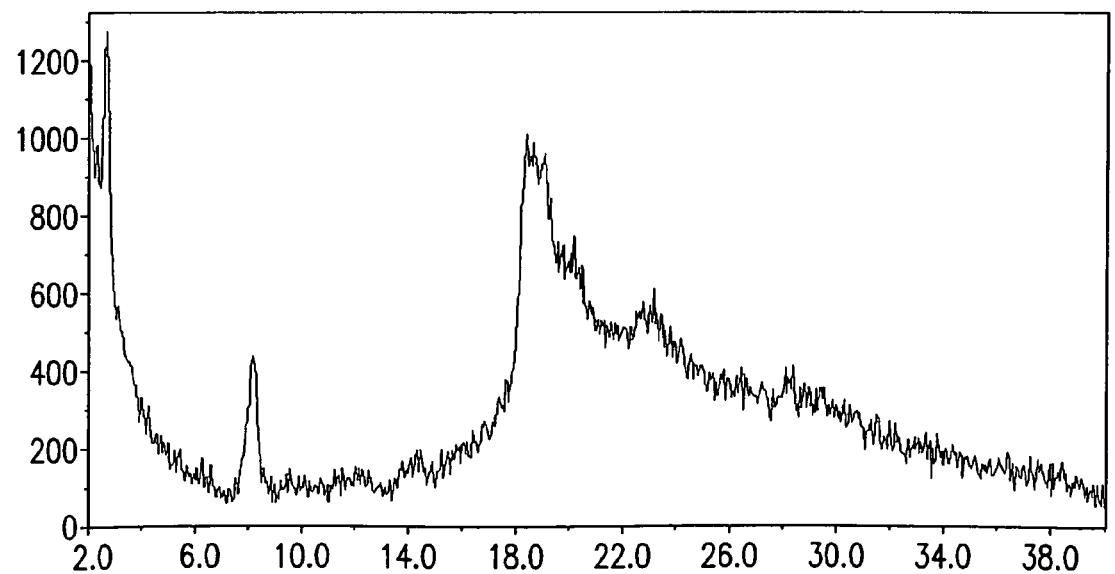
FIG. 4 is a characteristic powder X-ray diffraction pattern (XRPD) of atorvastatin potassium Form A (as prepared in Example 10).

The present invention relates to crystalline forms of atorvastatin potassium and novel processes for preparing crystalline forms of atorvastatin potassium.

In accordance with the invention, atorvastatin potassium can be prepared in different polymorphic forms. Polymorphism, the occurrence of different crystal forms, is a property of some molecules and molecular complexes. A single molecule, such as atorvastatin potassium may give rise to a variety of crystalline forms having distinct crystal structures and physical properties like melting point, X-ray diffraction pattern, infrared absorption fingerprint, and solid state NMR spectrum. One crystalline form may give rise to thermal behavior different from that of another crystalline form. Thermal behavior can be measured in the laboratory by such techniques as capillary melting point, thermogravimetric analysis ("TGA"), and differential scanning calorimetry ("DSC"), which have been used to distinguish polymorphic forms.

The difference in the physical properties of different crystalline forms results from the orientation and intermolecular interactions of adjacent molecules or complexes in the bulk solid. Accordingly, polymorphs are distinct solids sharing the same molecular formula, yet having distinct physical properties that can be advantageous in certain applications compared to other crystalline forms of the same compound or complex.

The crystalline forms of the present invention may be prepared from the following compound:

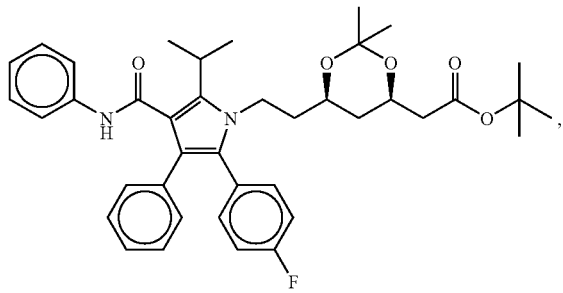

whose systematic chemical name is [R-(R*,R*)]-2-(4-fluorophenyl)-β,δ-dioxane-5-(1methylethyl)-3-phenyl-4-[(phenylamino carbonyl]-1H-pyrrole-1-tert-butylheptanoic ester, and which will hereafter be referred to as pyrrole acetonide ester or PAE.

Alternatively, the atorvastatin potassium crystalline forms of the present invention may be prepared from the lactone form of atorvastatin.

The atorvastatin used in any of the processes described in the present application can be in its lactone form or may be obtained by subjecting the PAE compound to conditions that cleave the acetonide and tert-butyl ester group to form atorvastatin.

Preferred conditions for cleaving the PAE compound employ aqueous hydrochloric acid, more preferably about 1.5% aqueous hydrochloric acid. The solution of atorvastatin thus produced, in either free acid or lactone form, or mixture thereof, is then treated with potassium hydroxide, preferably a modest excess thereof, more preferably about 1.5 equivalents with respect to the PAE.

After association of the atorvastatin with dissolved potassium derived from the added potassium hydroxide salt, any excess potassium hydroxide may be separated by filtration. The solution may then be evaporated until a precipitate forms. The isolated precipitate is crystalline.

The present invention provides a solid crystalline atorvastatin potassium, denominated as Form A, characterized by data selected from the group consisting of: an X-ray powder diffraction (XRPD) pattern having peaks at about 2.7 and 8.0±0.3 degrees 2θ and a broad peak with maximum at about 18.5±0.3 degrees 2θ, a solid-state $^{13}$C NMR spectrum with signals at about 126.5, 133.0 and 167.5±0.2 ppm, a solid-state $^{13}$C NMR spectrum having chemical shift differences between the signal exhibiting the lowest chemical shift and another signal in the chemical shift range of 100 to 200 ppm of about 10.9, 17.4 and 51.9±0.1 ppm wherein the lowest chemical shift in the chemical shift area of 100 to 200 ppm is at about 115.6±1 ppm, and combinations thereof.

Figure 5A:
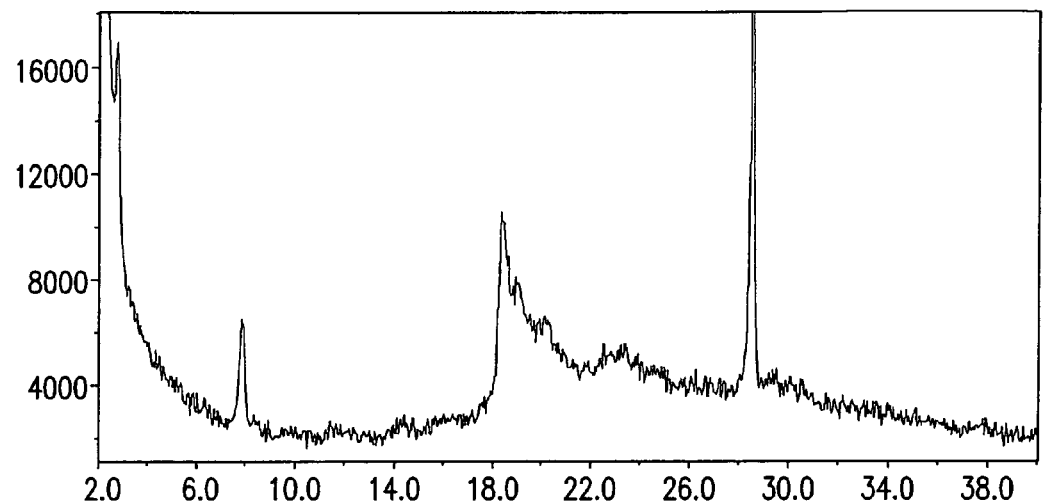
FIG. 5a is a characteristic powder X-ray diffraction pattern (XRPD) of atorvastatin potassium Form A (as prepared in Example 9, before re-crystallization). The peal at 28.5° is attributed to KCl.
Figure 5B:
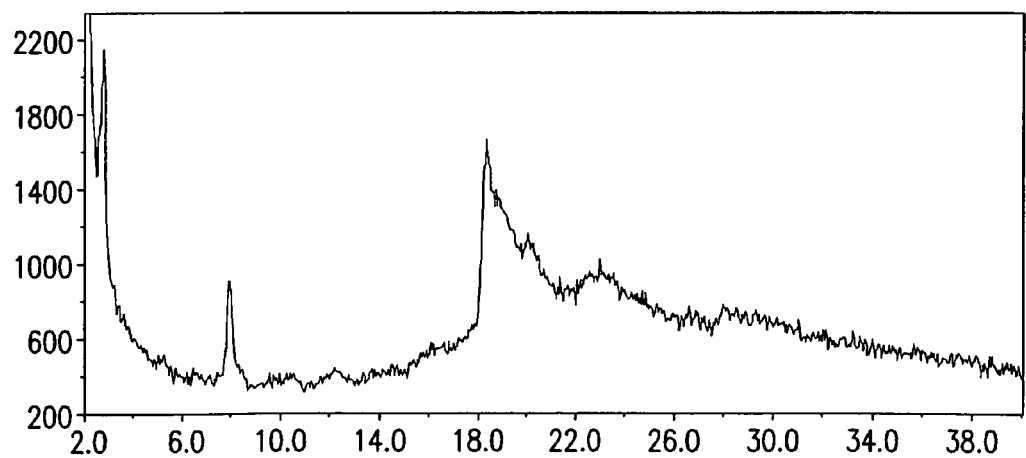
FIG. 5b is a characteristic powder X-ray diffraction pattern (XRPD) of atorvastatin potassium Form A (as prepared in Example 9 after re-crystallization).
Figure 6:
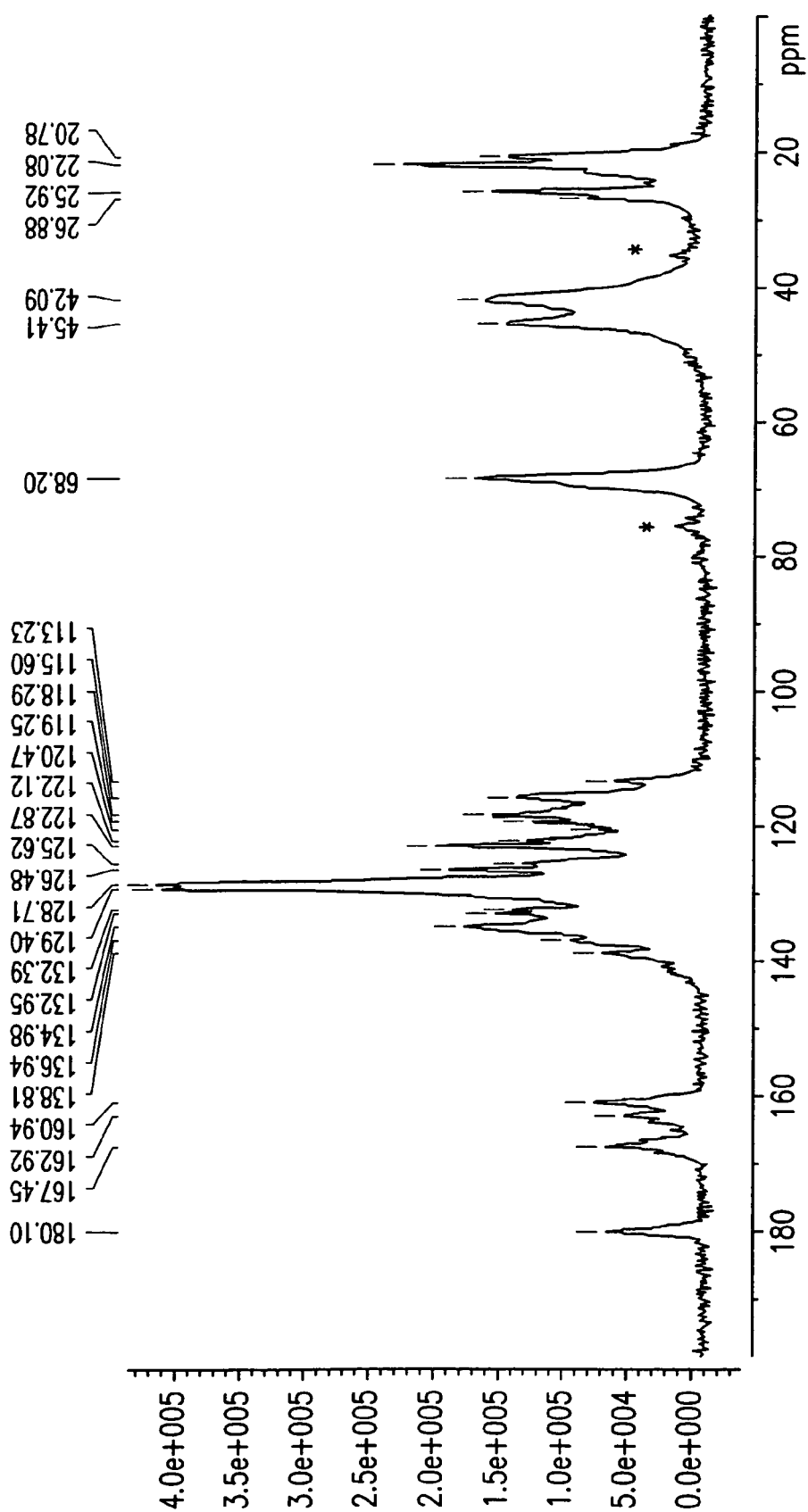
FIG. 6 is a solid-state $^{13}$C NMR spectrum of atorvastatin potassium Form A in the 0-200 ppm range.
Figure 7:
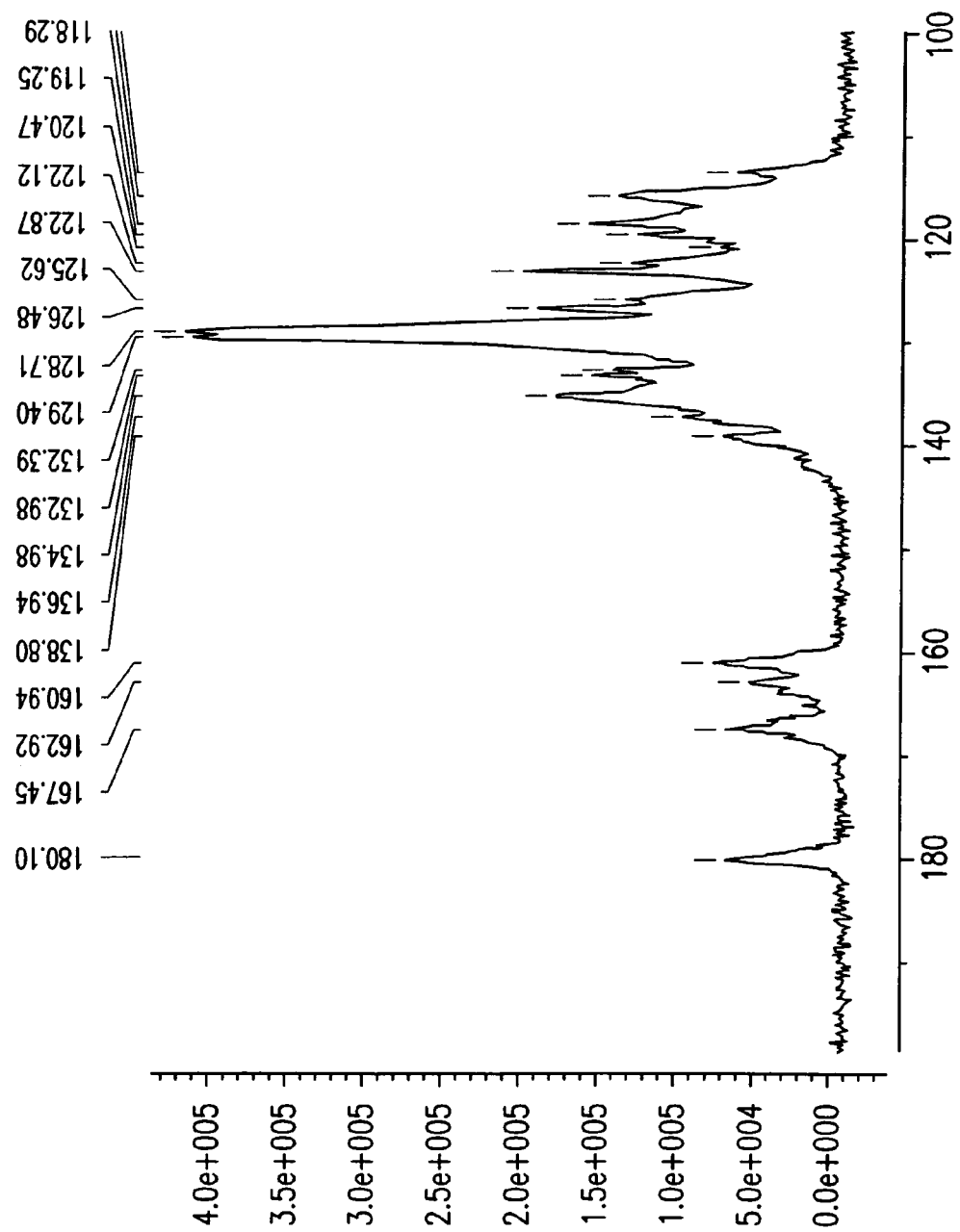
FIG. 7 is a solid-state $^{13}$C NMR spectrum of atorvastatin potassium Form A in the 100-200 ppm range.

Form A may be further characterized by an X-ray powder diffractogram as depicted in FIGS. 1-4, 5a and 5b and solid-state $^{13}$C NMR spectra as depicted in FIGS. 6 and 7.

Preferably, Form A described above is pure with respect to the amorphous form or other crystalline forms of atorvastatin potassium such as crystalline Form I and/or Form III. Preferably, in some preparations, Form A comprises less than 5% atorvastatin potassium crystalline Form I and/or Form III, more preferably less than 3%, and even more preferably less than 1%. In some preparations, Form A represents at least about 85%, 90%, 95%, or 99% by weight of all forms of atorvastatin potassium in the preparations.

In some preparations, Form A may also be characterized by having about 4.5% to about 26.4% water as determined by Karl Fisher (KF).

Another aspect of the present invention is a process for preparing atorvastatin potassium Form A. The method of preparing atorvastatin potassium Form A comprises providing a mixture of atorvastatin, THF or an ethanol:water mixture, and potassium hydroxide, and precipitating atorvastatin potassium Form A out of the reaction mixture by removing the solvent or by combining the mixture with an antisolvent that is a liquid $C_4$-$C_6$ ether or a $C_5$-$C_{10}$ alkane.

Preferably, the antisolvent is methyl tert butyl ether (MTBE) or heptane.

Preferably, when atorvastatin is prepared from the PAE compound, the solvent used in the process described above is an ethanol:water mixture.

Preferably, the ethanol:water mixture is used at a volume ratio of about 1:0.1 to about 1:0.25 (v/v) ml ethanol to ml water. More preferably, the ratio is about 1:0.15 to about 1:0.2 (v/v), and, most preferably, the ratio is 1:0.19 (v/v).

When atorvastatin is obtained from PAE, preferably PAE and potassium hydroxide are added at a ratio of about 1:0.01 to about 1:0.3 (w/w) of grams PAE to grams potassium hydroxide. More preferably, the ratio is about 1:0.15 to about 1:0.25 (w/w), and, most preferably, the ratio is 1:0.2 (w/w).

Preferably, when atorvastatin is prepared from its lactone form, the solvent used in the process described above is THF.

When atorvastatin is used in its lactone form, preferably atorvastatin lactone and potassium hydroxide are added at a ratio of about 1:0.1 to about 1:1.05 (w/w) of grams atorvastatin lactone to grams potassium hydroxide. More preferably, the ratio is about 1:0.15 to about 1:1 (w/w), and, most preferably, the ratio is 1:0.16 (w/w).

When atorvastatin is prepared from its lactone form, Form A is preferably precipitated out of the reaction by solvent removal. Preferably, solvent is removed by evaporation, more preferably under vacuum.

The process described above is preferably conducted at a temperature of about 25° C. to about 50° C., more preferably at about 35° C. to about 45° C., and most preferably at about 40° C.

Preferably, prior to addition of the antisolvent, the reaction mixture is filtered.

Following the addition of the antisolvent, the reaction mixture is preferably cooled to a temperature of about 2° C. to about 20° C., more preferably to about 5° C. to about 15° C., and most preferably to about 5° C.

Re-crystallization under the same conditions can be performed to remove KCl excess.

Yet another aspect of the present invention is a process for preparing atorvastatin potassium Form A. The method of preparing atorvastatin potassium Form A comprises providing a mixture of atorvastatin, THF or 2-methyl THF, water and potassium hydroxide, and precipitating atorvastatin potassium Form A out of the reaction mixture by evaporation.

Preferably, evaporation is performed under vacuum.

Optionally, an antisolvent that is a liquid $C_4$-$C_6$ ether is added to the evaporated reaction mixture. Preferably, the $C_4$-$C_6$ ether is methyl tert butyl ether (MTBE).

The volume ratio between the THF or 2-methyl THF and water in the above reaction mixture is preferably between about 10:0.5 to about 10:2 (v/v) of ml THF or 2-methyl THF to ml water. More preferably, it is about 10:1.5 (v/v).

Preferably, atorvastatin in the process described above is in its lactone form.

Preferably, atorvastatin lactone and potassium hydroxide are added at a ratio of about 1:0.1 to about 1:1 (w/w) of grams atorvastatin lactone to grams potassium hydroxide. More preferably, the ratio is about 1:0.1 to about 1:0.5 (w/w), and, most preferably, the ratio is about 1:0.11 (w/w).

The process described above is preferably conducted at a temperature of about 25° C. to about 50° C., more preferably at about 35° C. to about 45° C., and most preferably at about 40° C.

Preferably, prior to addition of MTBE, the reaction mixture is filtered.

Following the addition of MTBE, the reaction mixture is preferably cooled to a temperature of about 2° C. to about 20° C., more preferably to about 5° C. to about 15° C., and most preferably to about 5° C.

In one specific embodiment, atorvastatin lactone, THF, water and potassium hydroxide are combined at a temperature of about 1° C. to about 10° C., preferably at about 4° C., and, following filtration, the reaction mixture is heated to a temperature of about 40° C., prior to addition of MTBE at a temperature of about 10° C. to about 20° C., preferably about 15° C., followed by a cooling step to a temperature of about 5° C. to allow precipitation of atorvastatin potassium Form A. Preferably, following the initial precipitation, an additional amount of MTBE is added to the reaction mixture at a temperature of about 15° C. to about 25° C., preferably about 20° C., followed by another cooling step to a temperature of about 5° C., and the obtained crystalline form is exposed to about 60%-80% relative humidity at about 40° C. to remove residual solvent.

The present invention further encompasses a crystalline form of atorvastatin potassium, denominated as Form B, characterized by data selected from the group consisting of: an X-ray powder diffraction (XRPD) pattern having peaks at about 8.8, 19.0 and 20.5±0.3 degrees 2θ, and at least two peaks selected from the group consisting of 7.7, 9.8, 21.6, 23.9 and 26.9±0.3 degrees 2θ, an XRPD pattern having peaks at about 8.8, 19.0, 20.5, 23.9, and 26.9±0.3 degrees 2θ, a solid-state $^{13}$C NMR spectrum with signals at about 129.2, 166.2 and 177.2±0.2 ppm, a solid-state $^{13}$C NMR spectrum having chemical shift differences between the signal exhibiting the lowest chemical shift and another signal in the chemical shift range of 100 to 200 ppm of about 11.6, 48.6 and 59.6±0.1 ppm wherein the lowest chemical shift in the chemical shift area of 100 to 200 ppm is at about 117.6±1 ppm, and combinations thereof.

The above crystalline Form B may be further characterized by an XRPD pattern having peaks at about: 7.7, 8.8, 9.8, 12.3, 15.9, 19.0, 20.5, 21.6, 23.9 and 26.9±0.3 degrees 2θ.

Figure 8:
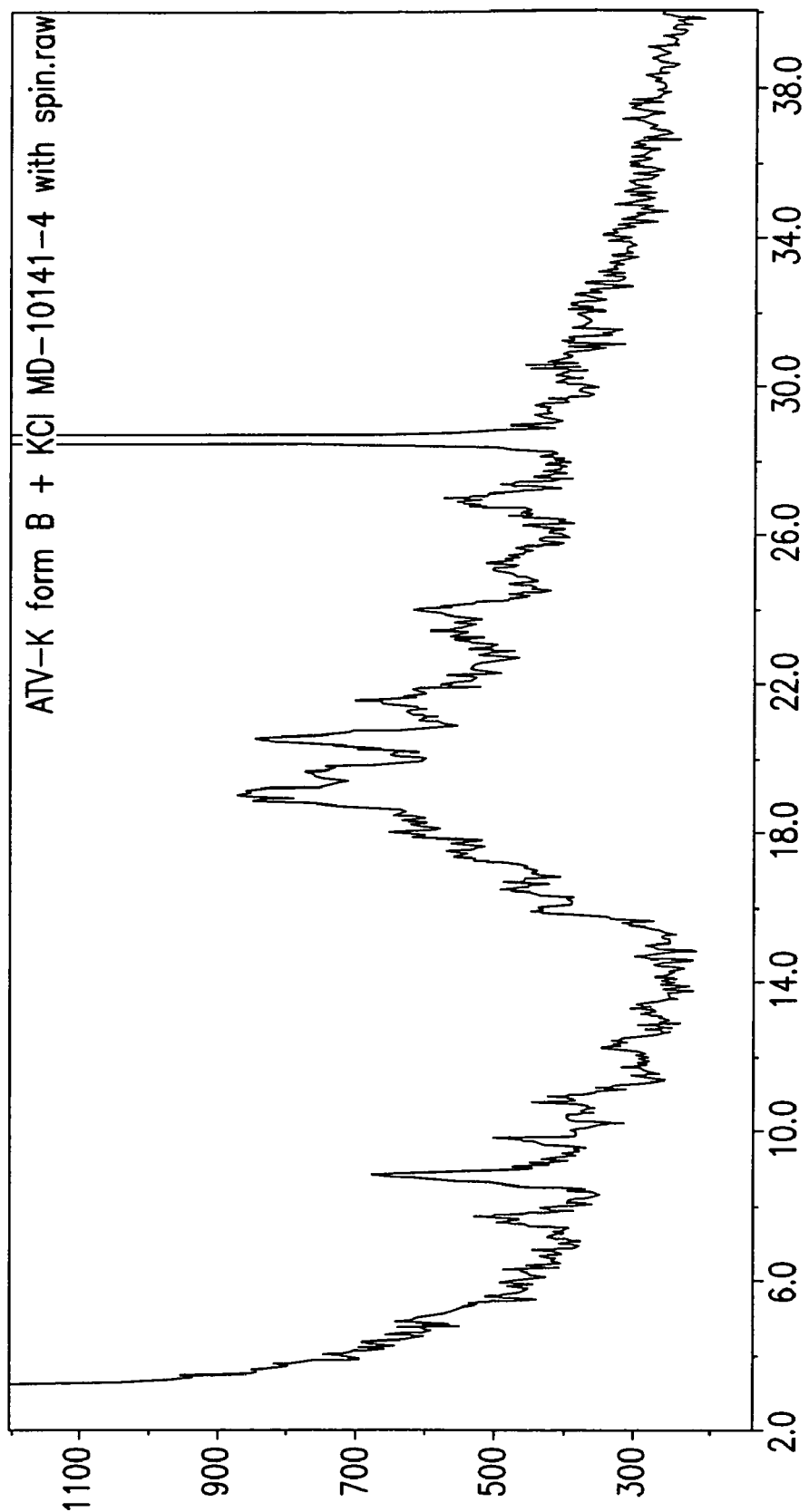
FIG. 8 is a characteristic powder X-ray diffraction pattern (XRPD) of atorvastatin potassium Form B (as prepared in Example 11). The peak at 28.5° is attributed to KCl.
Figure 9:
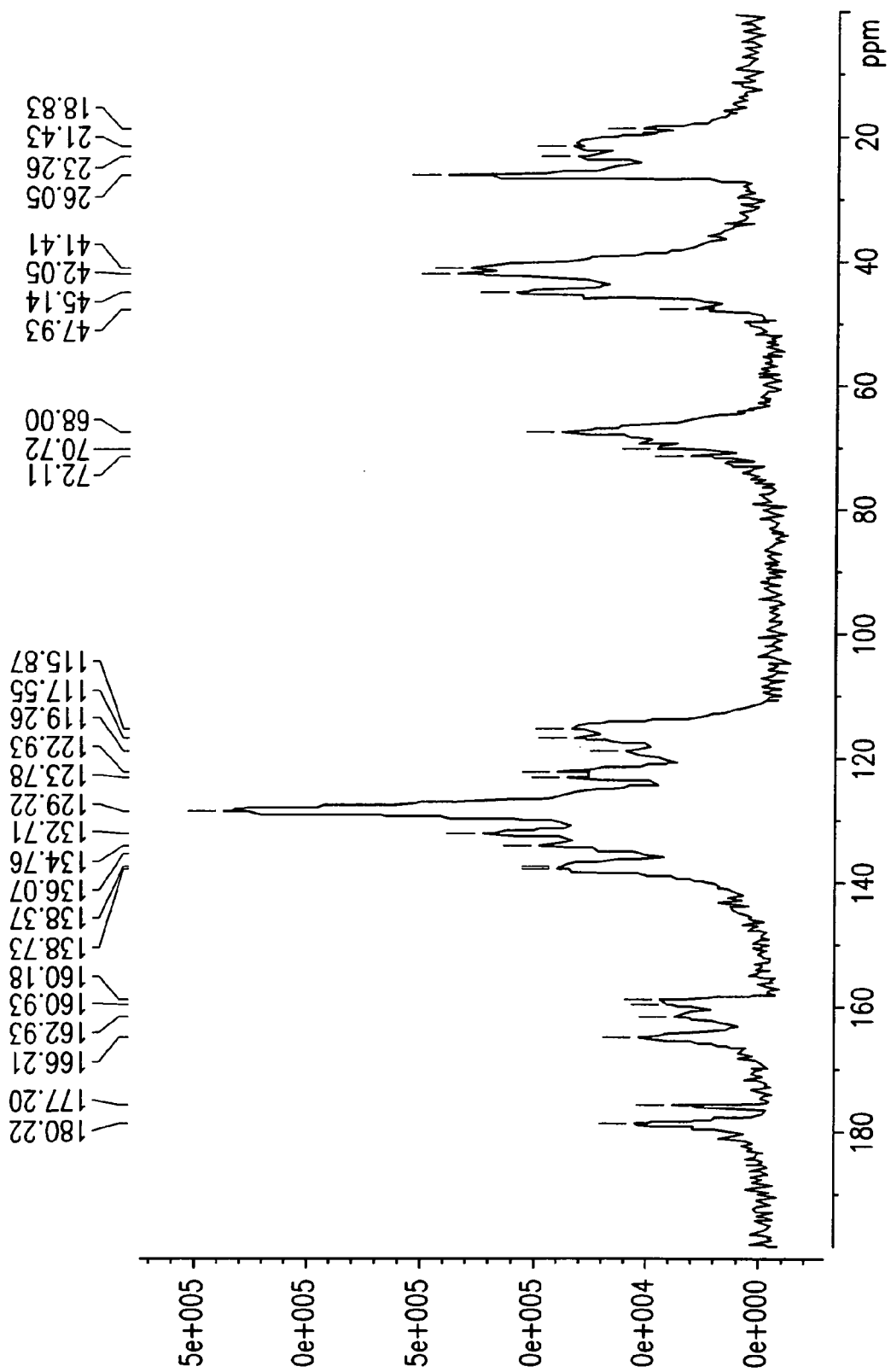
FIG. 9 is a solid-state $^{13}$C NMR spectrum of atorvastatin potassium form B in the 0-200 ppm range.
Figure 10:
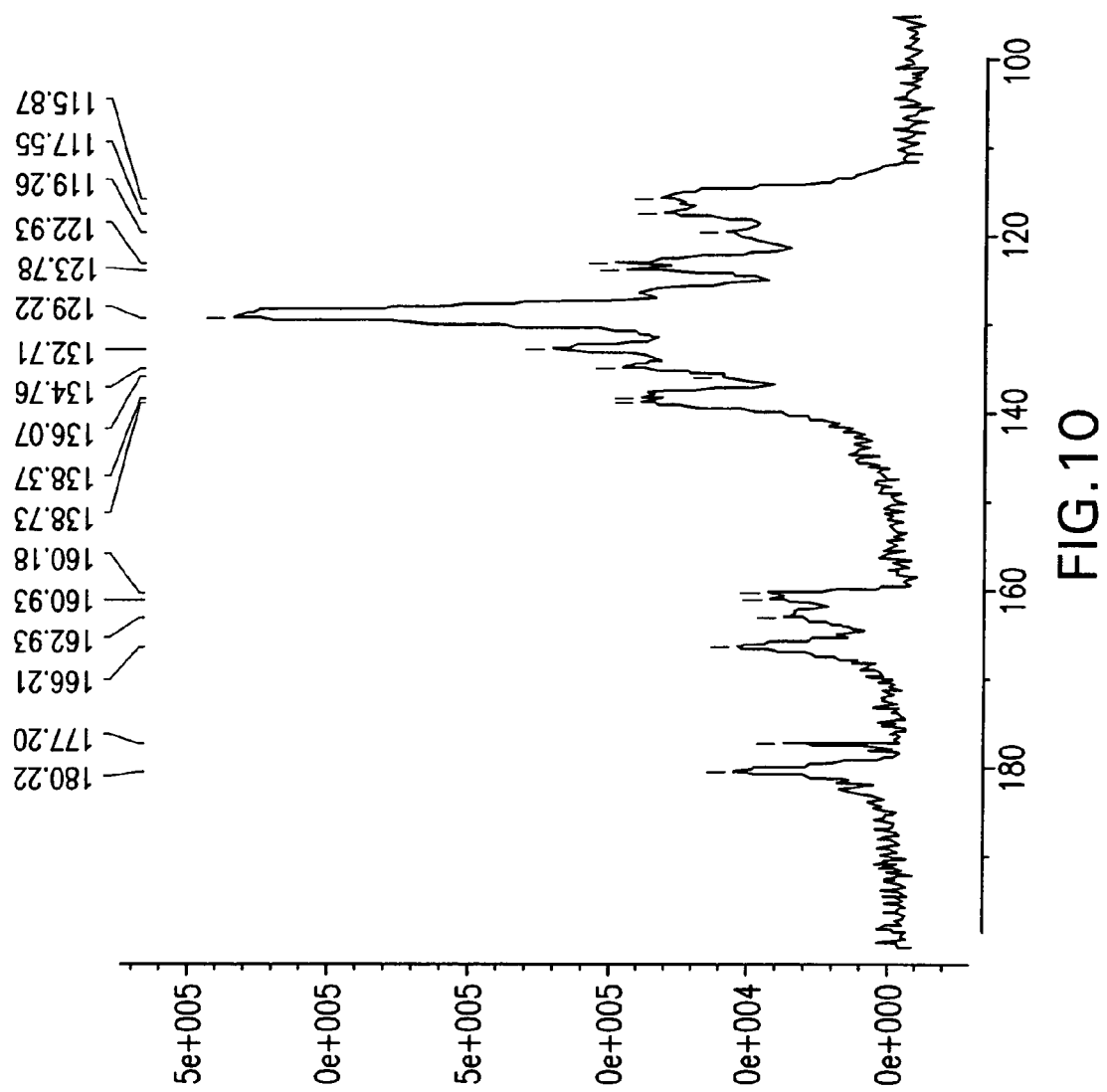
FIG. 10 is a solid-state $^{13}$C NMR spectrum of atorvastatin potassium Form B in the 100-200 ppm range.

Form B may be further characterized by an X-ray powder diffractogram as depicted in FIG. 8 and solid-state $^{13}$C NMR spectra as depicted in FIGS. 9 and 10.

Form B may be also characterized by having about 12% weight loss at the range of 30-200° C. as determined by TGA at a heating rate of about 10° C./min.

Another aspect of the present invention is a process for preparing atorvastatin potassium Form B. The method of preparing atorvastatin potassium Form B comprises providing a mixture of atorvastatin, ethanol and potassium hydroxide, and precipitating atorvastatin potassium Form B out of the reaction mixture by combining the reaction mixture with an antisolvent that is a $C_6$-$C_{10}$ aromatic hydrocarbon.

Preferably the aromatic hydrocarbon is toluene.

Preferably, the atorvastatin used in the process described above is prepared from the PAE compound.

Preferably, PAE and potassium hydroxide are added at a ratio of about 1:0.1 to about 1:0.85 (w/w) of grams PAE to grams potassium hydroxide. More preferably, the ratio is about 1:0.1 to about 1:0.5 (w/w) and, most preferably, it is about 1:0.22 (w/w).

The process described above is preferably conducted at a temperature of about 25° C. to about 50° C., more preferably at about 35° C. to about 45° C., and most preferably at about 40° C.

Preferably, prior to addition of toluene, the reaction mixture is filtered.

Toluene is preferably added while the reaction mixture is at a temperature of about 2° C. to about 20° C., more preferably about 5° C. to about 15° C., and most preferably about 5° C.

Described below is a crystalline form of atorvastatin potassium, denominated as Form III, characterized by data selected from the group consisting of an X-ray powder diffraction (XRPD) pattern having peaks at about: 7.8, 16.6, 19.6±0.3 degrees 2θ, and at least two peaks selected from the group consisting of 2.8, 4.9, 18.6, 21.6 and 29.1±0.3 degrees 2θ, a solid-state $^{13}$C NMR spectrum with signals at about 165.9, 138.7 and 126.8±0.2 ppm, a solid-state $^{13}$C NMR spectrum having chemical shift differences between the signal exhibiting the lowest chemical shift and another signal in the chemical shift range of 100 to 200 ppm of about 50.7, 23.5 and 11.6±0.1 ppm wherein the signal exhibiting the lowest chemical shift in the chemical shift area of 100 to 200 ppm is at about 115.2±1 ppm, and combinations thereof.

Figure 11:
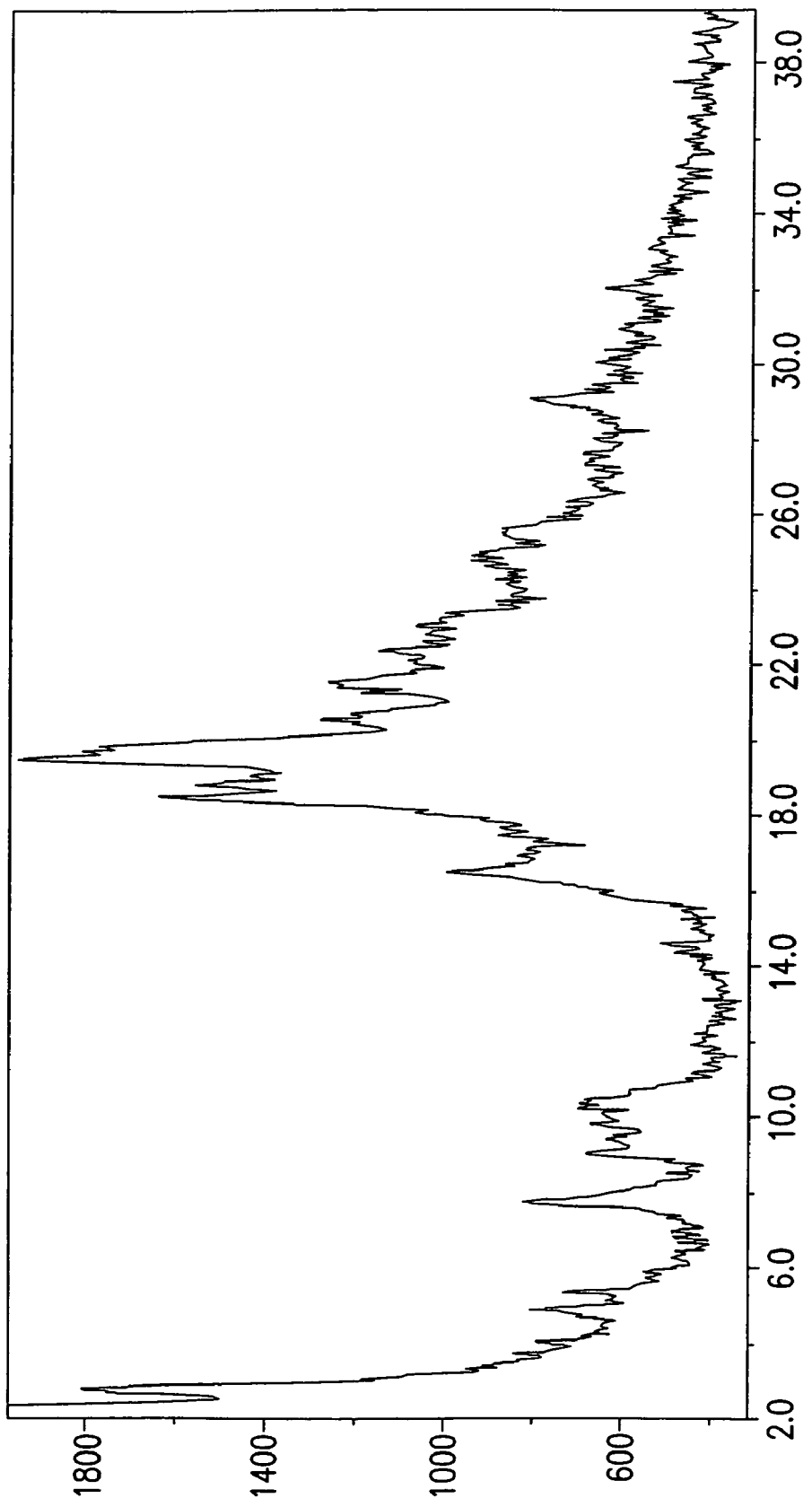
FIG. 11 is a characteristic powder X-ray diffraction pattern (XRPD) of atorvastatin potassium Form III (as prepared in Example 12).
Figure 12:
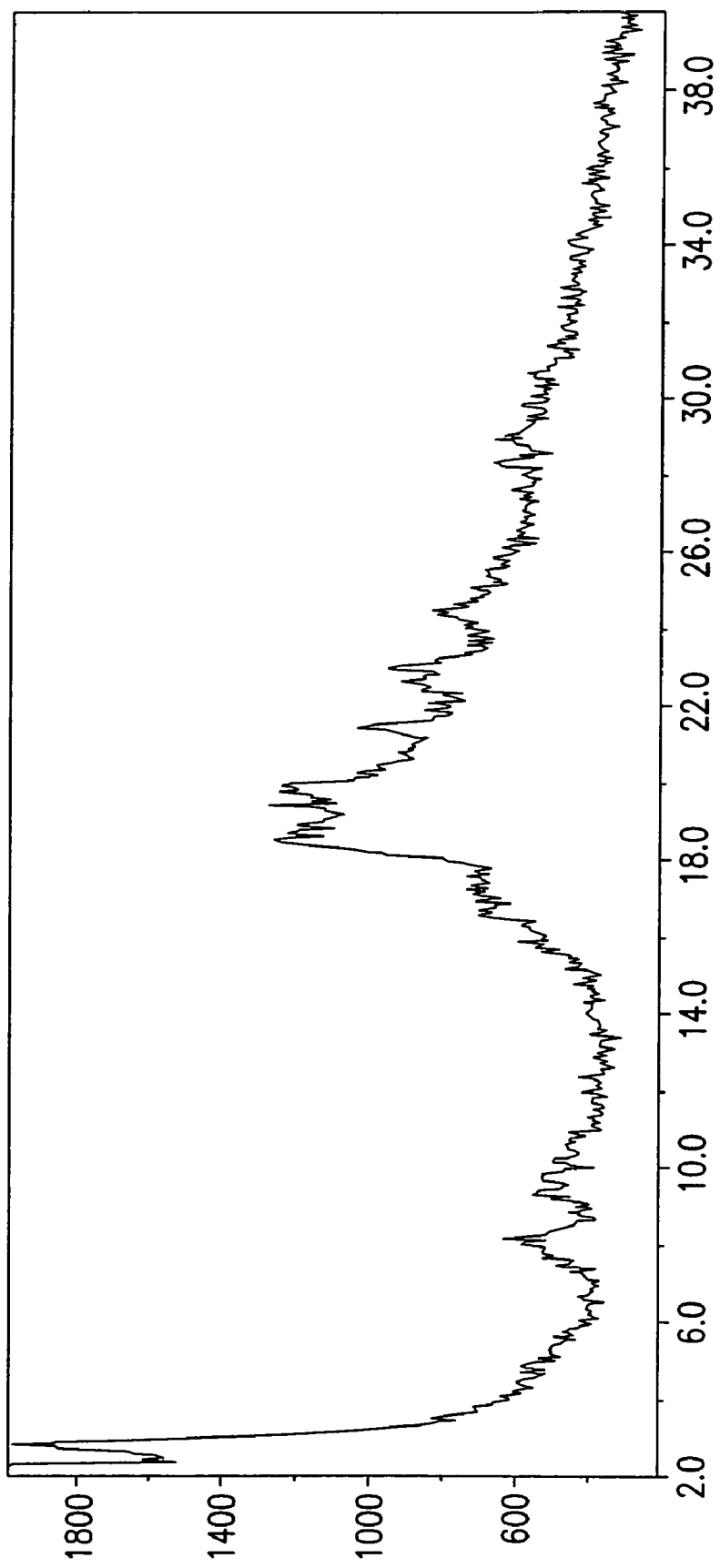
FIG. 12 is a characteristic powder X-ray diffraction pattern (XRPD) of atorvastatin potassium Form III (as prepared in Example 13).
Figure 13:
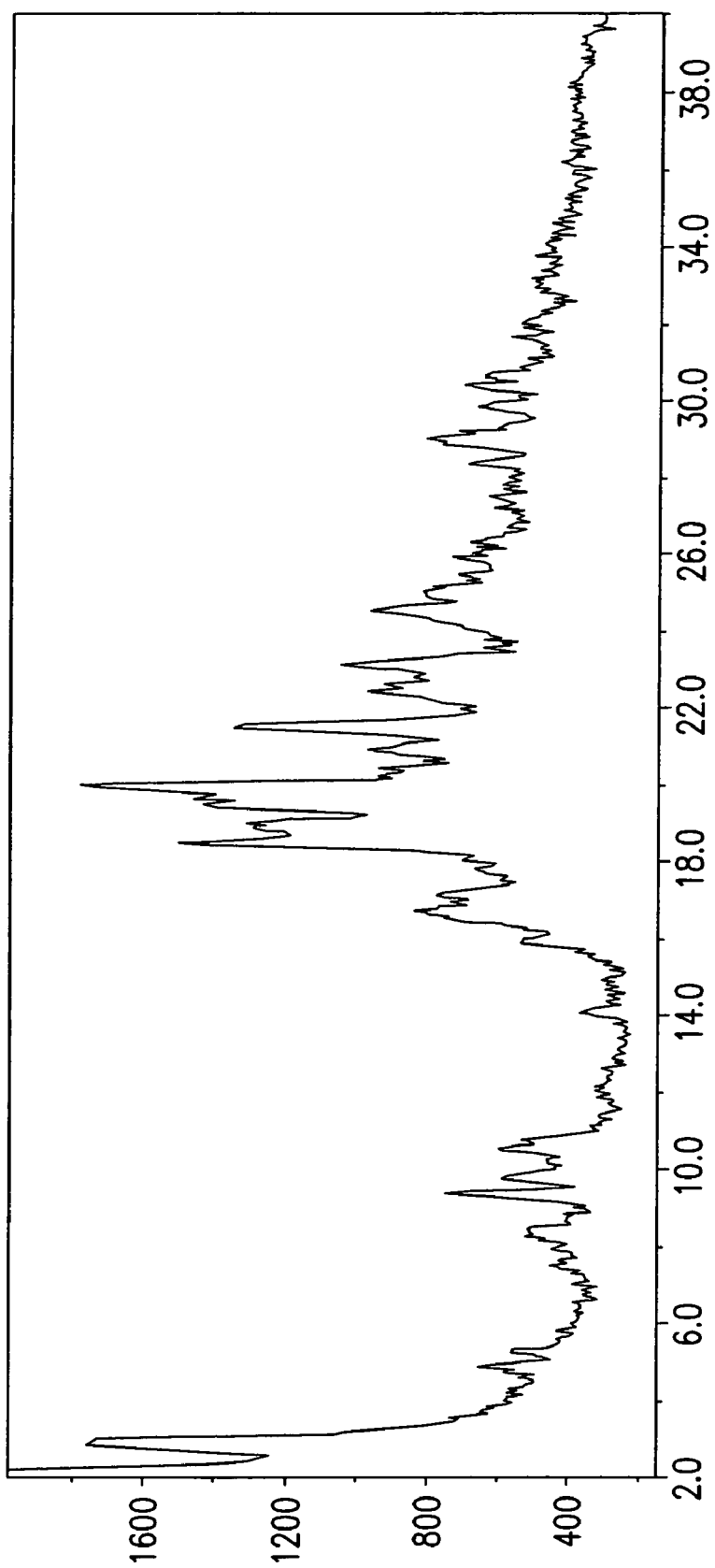
FIG. 13 is a characteristic powder X-ray diffraction pattern (XRPD) of atorvastatin potassium Form III (as prepared in Example 14).
Figure 14:
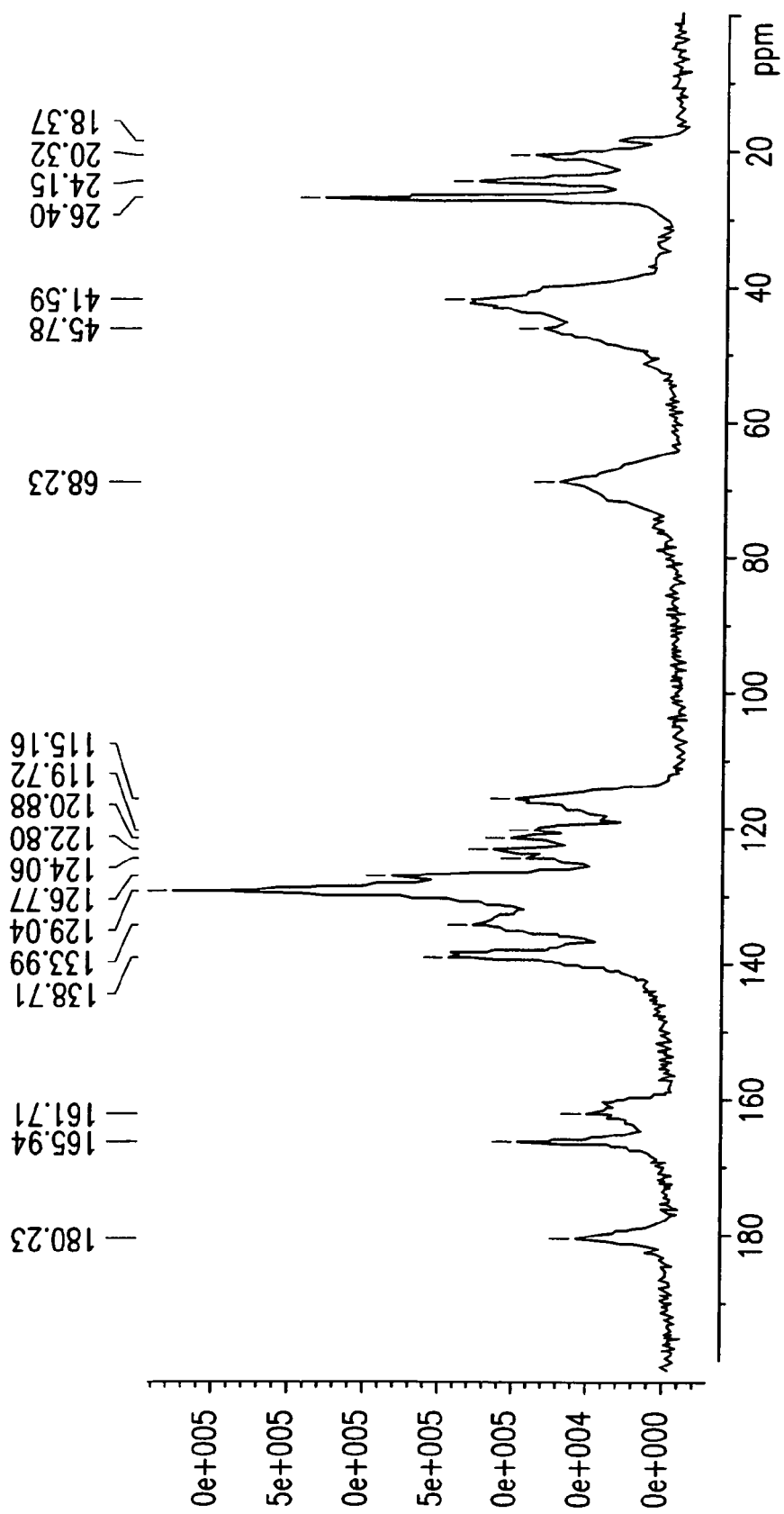
FIG. 14 is a solid-state $^{13}$C NMR spectrum of atorvastatin potassium Form III in the 0-200 ppm range.
Figure 15:
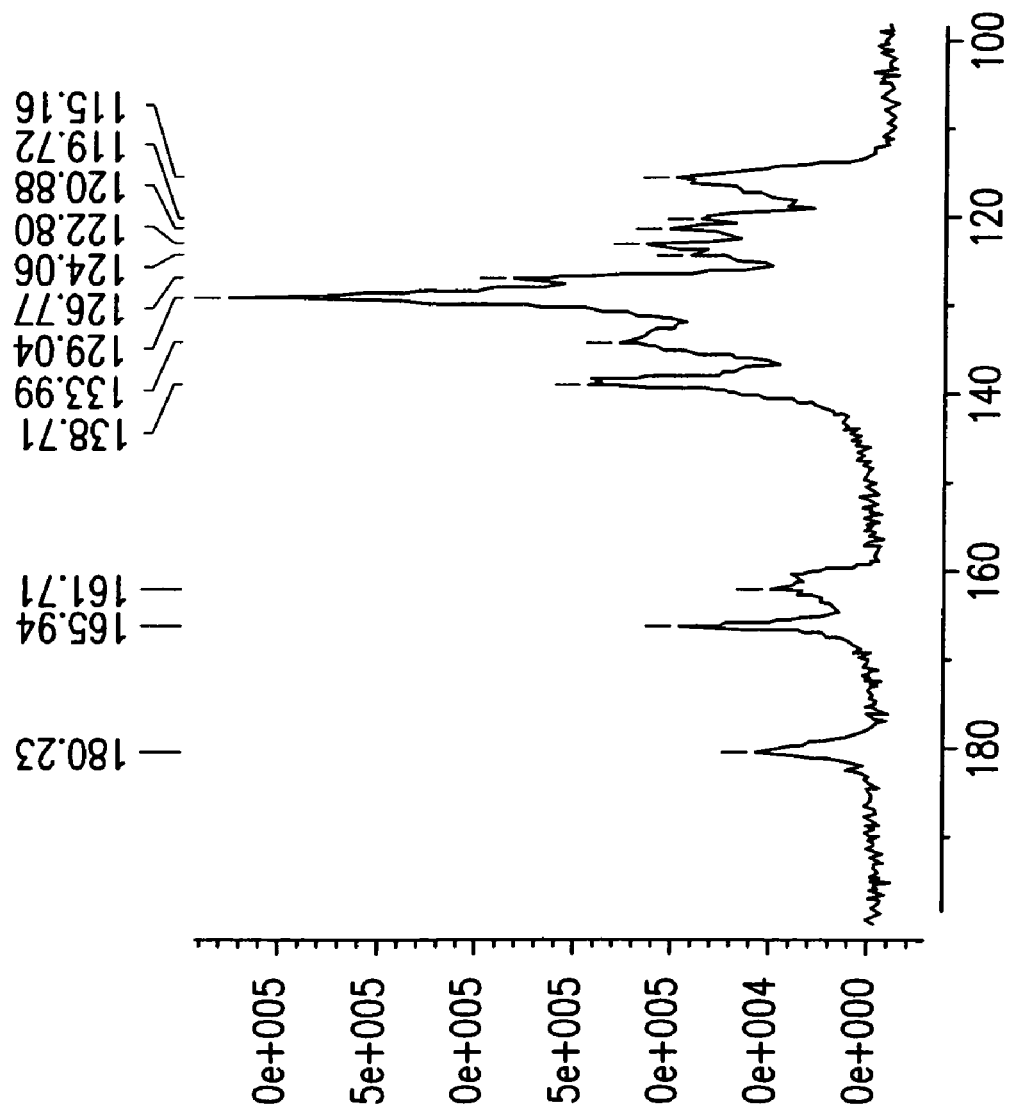
FIG. 15 is a solid-state $^{13}$C NMR spectrum of atorvastatin potassium Form III in the 100-200 ppm range.

Form III may be further characterized by X-ray powder diffractograms as depicted in FIGS. 11-13 and solid-state $^{13}$C NMR spectra as depicted in FIGS. 14 and 15.

Form III is also characterized by having about 8.8% weight loss in the range of 30° C.-190° C. as determined by TGA at a heating rate of about 10° C./min.

Another aspect of the present invention is a process for preparing atorvastatin potassium Form III. The method of preparing atorvastatin potassium Form III comprises providing a mixture of atorvastatin, isopropanol and potassium hydroxide, and precipitating atorvastatin potassium Form III out of the reaction mixture by removing the solvent.

Preferably, the atorvastatin used in the process described above is in its lactone form.

Preferably, atorvastatin and potassium hydroxide are added at a ratio of about 1:0.1 to about 1:1.1 (w/w) of grams atorvastatin to grams potassium hydroxide. More preferably, the ratio is about 1:0.1-1:0.5 (w/w), and, most preferably, the ratio is about 1:0.1 (w/w).

The process described above is preferably conducted at a temperature of about 30° C. to about 50° C., more preferably at about 40° C. to about 50° C., and even more preferably at about 45° C.

The atorvastatin starting material in any of the above described processes can be in its free acid form or in its lactone form.

A further aspect of the present invention is a process for preparing atorvastatin potassium Form III comprising suspending atorvastatin potassium Form A in ethanol.

Preferably, the atorvastatin Form A and ethanol are added at a ratio of about 1:10 to about 1:20 (w/v) of grams Form A to ml ethanol. More preferably, the ratio is about 1:12 to about 1:17 (w/v) and, most preferably, the ratio is 1:15 (w/v).

The process described above is preferably conducted at a temperature of about 30° C. to about 50° C., more preferably at about 35° C. to about 45° C., and even more preferably at about 40° C.

Any excess potassium hydroxide may be separated by filtration. The solution may then be evaporated until a precipitate forms. The isolated precipitate obtained in the process described above can be further recovered by conventional techniques, such as filtration and drying, preferably under vacuum.

Described below is a crystalline form of atorvastatin potassium, denominated as Form I, characterized by data selected from the group consisting of an X-ray powder diffraction (XRPD) pattern having peaks at about: 3.1, 3.5, 5.1, 8.5 and 11.3±0.2 degrees 2θ, a solid-state $^{13}$C NMR spectrum with signals at about 181.6, 179.3 and 1161.0±0.2 ppm, a solid-state $^{13}$C NMR spectrum having chemical shift differences between the signal exhibiting the lowest chemical shift and another signal in the chemical shift range of 100 to 200 ppm of about 64.9, 62.6 and 44.3±0.1 ppm wherein the signal exhibiting the lowest chemical shift in the chemical shift area of 100 to 200 ppm is at about 116.7±1 ppm, and combinations thereof.

Form I may be further characterized by an X-ray powder diffraction (XRPD) pattern having peaks at about: 3.1, 3.5, 5.1, 8.5, 9.1, 10.6, 11.3, 18.2, 20.1 and 21.1±0.2 degrees 2θ.

Figure 16:
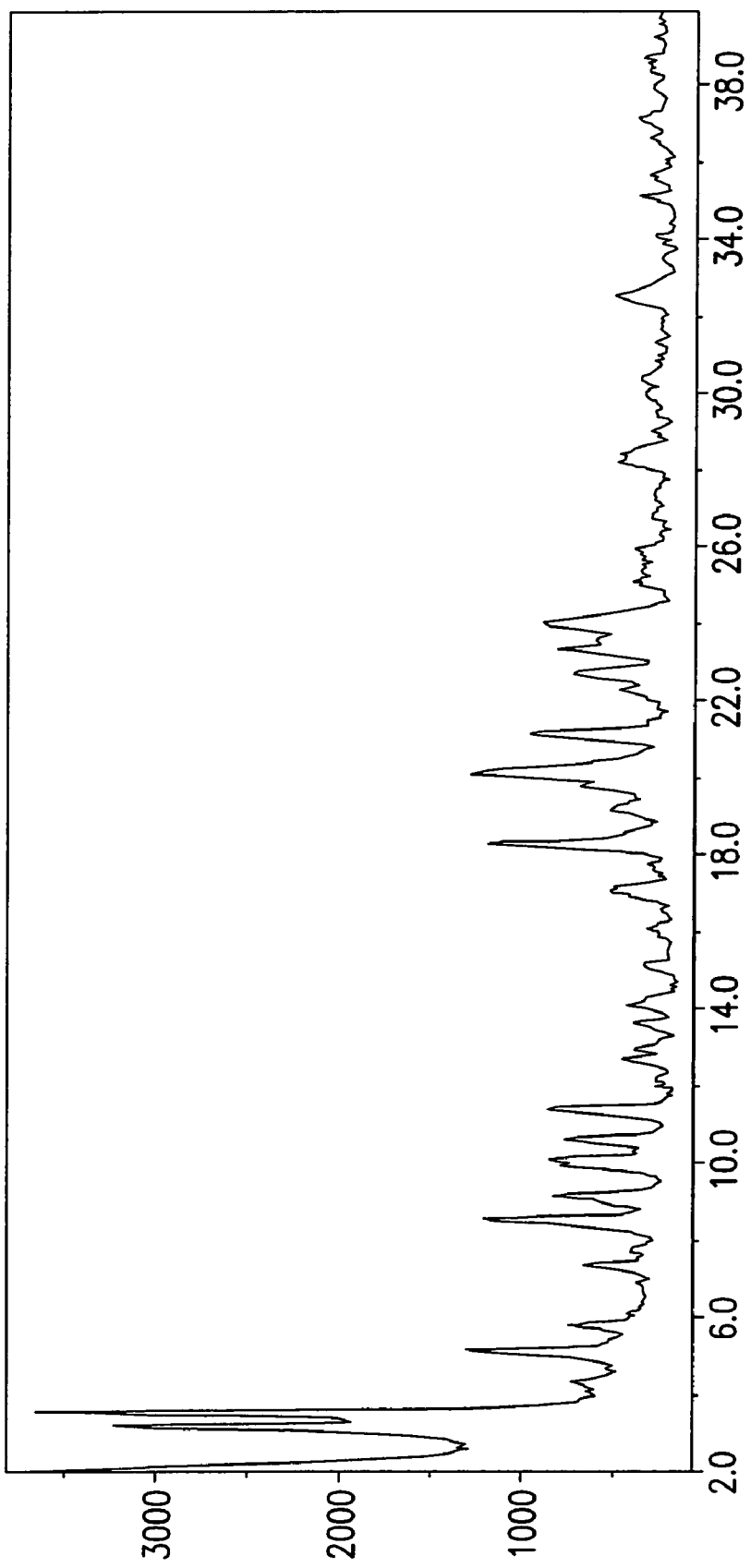
FIG. 16 is a characteristic powder X-ray diffraction pattern (XRPD) of atorvastatin potassium Form I (as prepared in Example 15).
Figure 17:
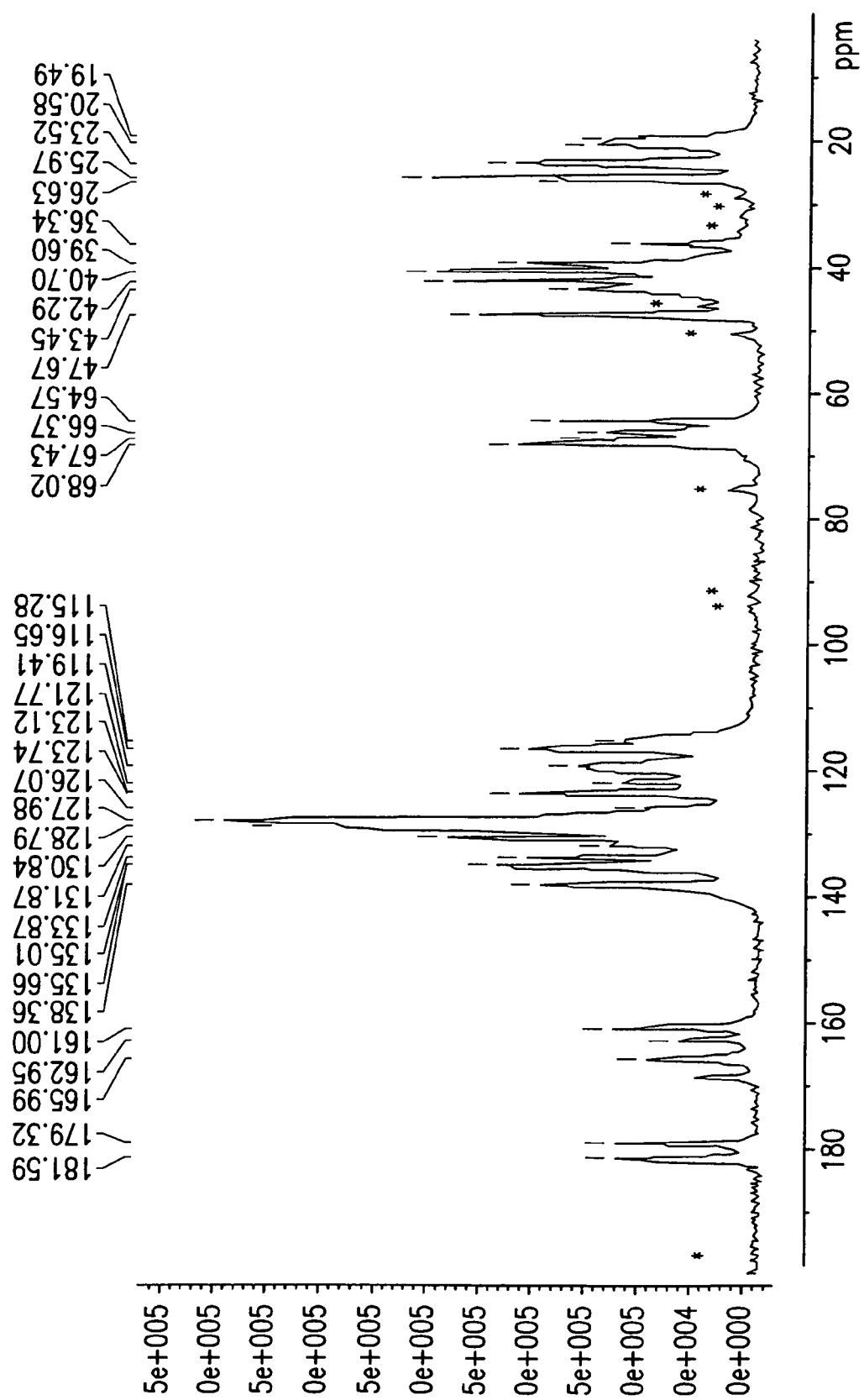
FIG. 17 is a solid-state $^{13}$C NMR spectrum of atorvastatin potassium Form I in the 0-200 ppm range.
Figure 18:
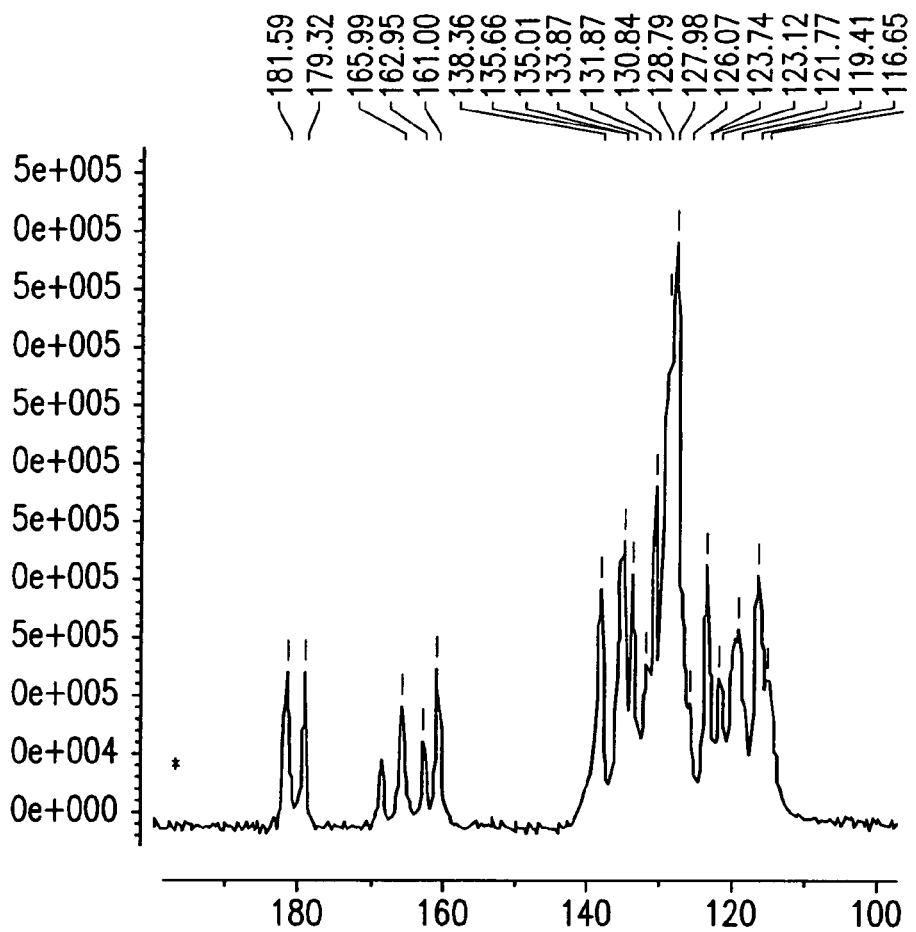
FIG. 18 is a solid-state $^{13}$C NMR spectrum of atorvastatin potassium Form I in the 100-200 ppm range.

Form I may also be characterized by an X-ray powder diffractogram as depicted in FIG. 16 and solid-state $^{13}$C NMR spectra as depicted in FIGS. 17 and 18.

Described herein is a process for preparing atorvastatin potassium Form I. The method of preparing atorvastatin potassium Form I comprises combining atorvastatin potassium Form A with ethanol to obtain a reaction mixture, precipitating atorvastatin potassium Form I out of the reaction mixture by combining the reaction mixture with an antisolvent that is a liquid $C_1$-$C_6$ ether such as MTBE, and filtering. Optionally, the filtering steps are done immediately after addition of the antisolvent.

The precipitate obtained in any of the processes described above can be further recovered by conventional techniques, such as filtration and drying, preferably under vacuum. Drying may also be carried out using a fluidized bed dryer fed with ambient air or dry $N_2$.

Removal of the solvent in any of the processes described above can be done by evaporation, preferably under vacuum.

Any excess water may be distilled out prior to combining with potassium hydroxide and/or prior to combining with the antisolvent.

Potassium hydroxide used in any of the processes described above is preferably in a solid form.

As used herein, a "drop" of water or ethanol refers to about 1 ml to about 2 ml of water or about 1 ml to about 2 ml of ethanol.

Figure 19:
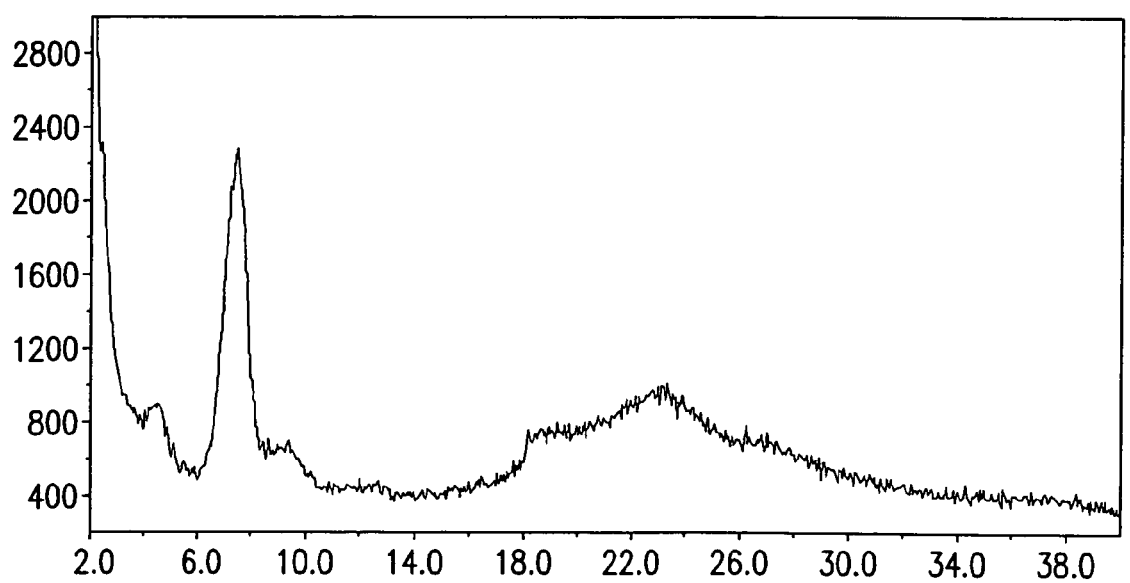
FIG. 19 is a characteristic powder X-ray diffraction pattern (XRPD) of atorvastatin potassium Form E (as prepared in Example 16)

The present invention further encompasses a crystalline form of atorvastatin potassium, denominated as Form E, characterized by an X-ray powder diffraction (XRPD) pattern having peaks at about 4.5, 6.5-8.3 (broad peak) and 9.2±0.3 degrees 2θ as depicted in FIG. 19.

Another aspect of the present invention is a process for preparing atorvastatin potassium Form E. The method of preparing atorvastatin potassium Form E comprises grinding atorvastatin potassium Form A, in the presence of water.

Preferably, about 1 to about 5 drops of water is used in the above described process. More preferably, about 2 to about 4 drops, or about 2 to about 3, drops of water is used. Preferably, about 1, 2, 3, 4, or 5 drops of water (i.e., about 1, 2, 3, 4, 5, 6, 7, 8, 9, or 10 ml of water) is used per 200 mg of atorvastatin potassium Form A.

Figure 20:
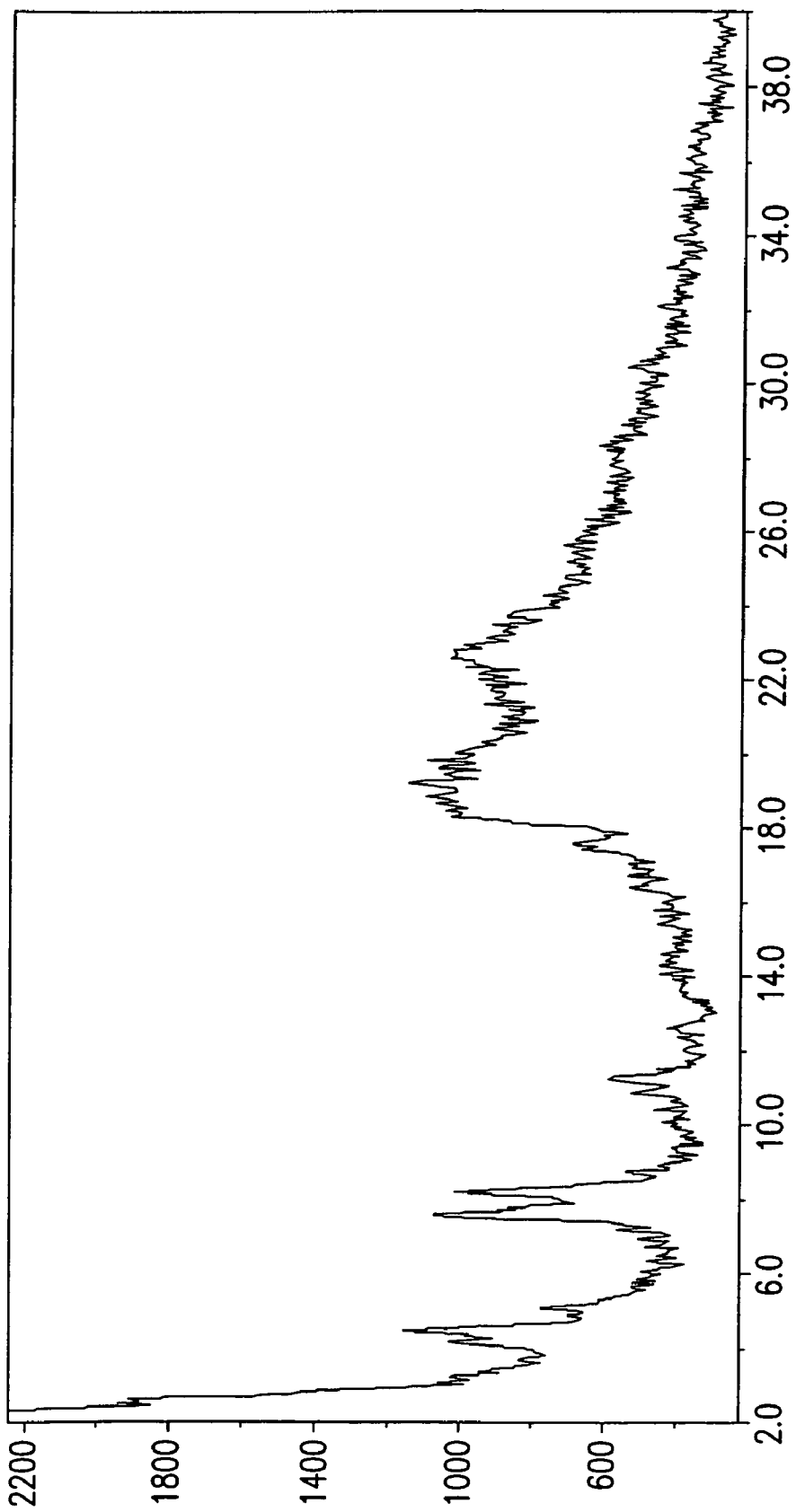
FIG. 20 is a characteristic powder X-ray diffraction pattern (XRPD) of atorvastatin potassium Form F (as prepared in Example 17)

The present invention further encompasses a crystalline form of atorvastatin potassium, denominated as Form F, characterized by an X-ray powder diffraction (XRPD) pattern having peaks at about 4.5, 5.1, 7.6, 11.2 and 17.6±0.2 degrees 2θ, as depicted in FIG. 20.

Another aspect of the present invention is a process for preparing atorvastatin potassium Form F. The method of preparing atorvastatin potassium Form F comprises grinding atorvastatin potassium Form A in the presence of ethanol.

Preferably, 96% ethanol is used in the process described above. In certain embodiments, absolute ethanol is used.

Preferably, about 1 to about 5 drops of ethanol is used in the above described process. More preferably, about 2 to about 4, or about 2 to about 3, drops of ethanol is used. Preferably, about 1, 2, 3, 4, or 5 drops of ethanol (i.e., about 1, 2, 3, 4, 5, 6, 7, 8, 9, or 10 ml of ethanol) is used per 200 mg of atorvastatin potassium Form A.

Figure 22:
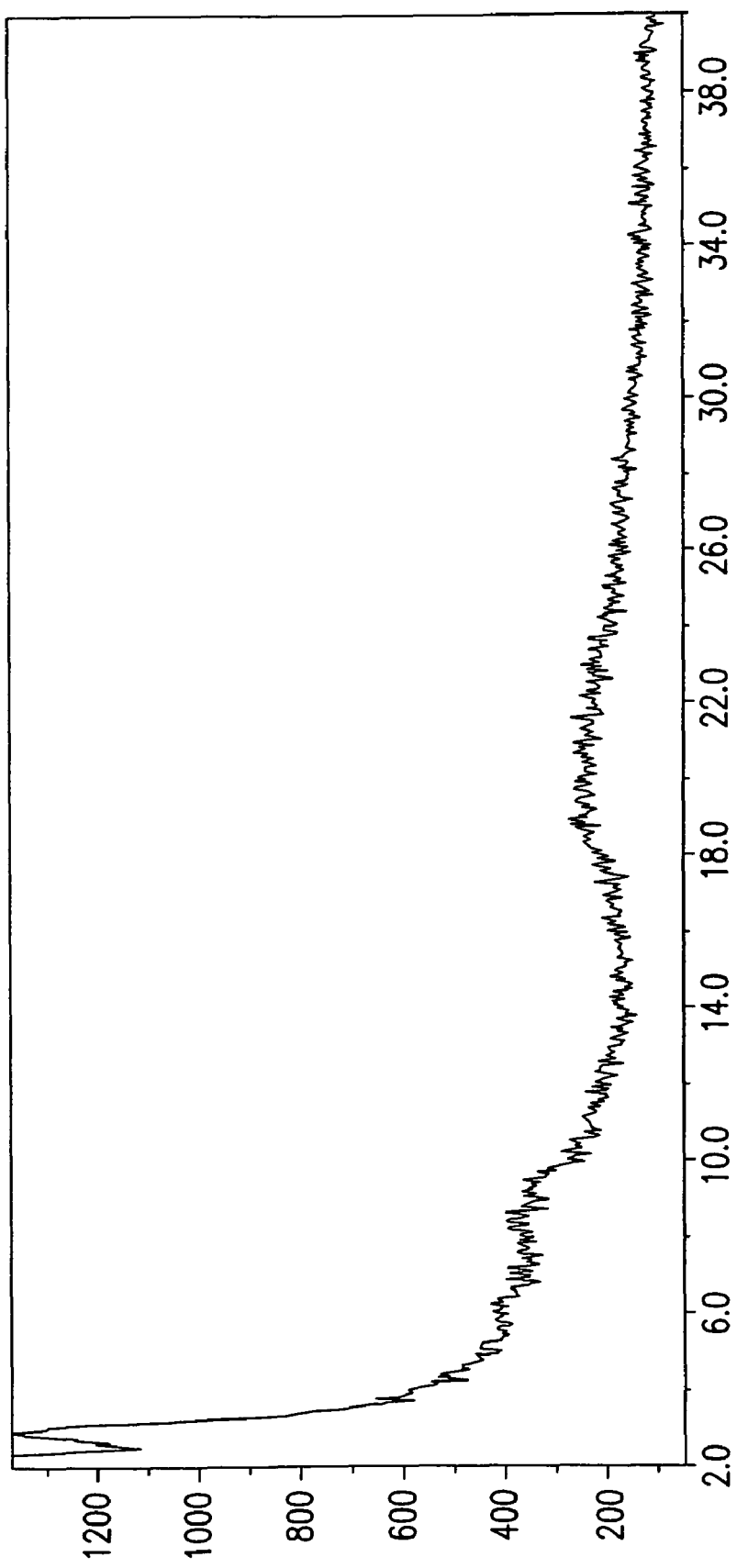
FIG. 22 is a characteristic powder X-ray diffraction pattern (XRPD) of amorphous atorvastatin potassium (as prepared in Example 20).
Figure 23:
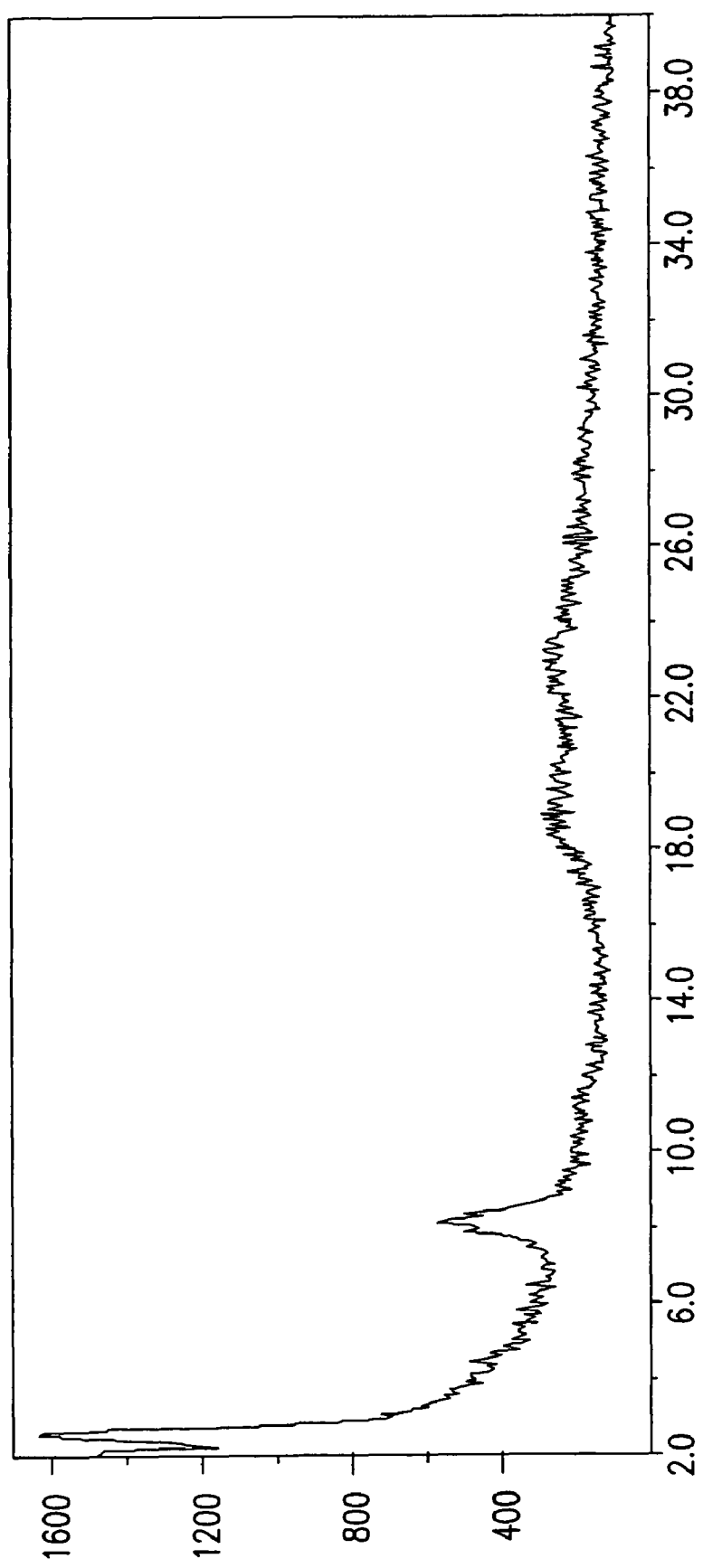
FIG. 23 is a characteristic powder X-ray diffraction pattern (XRPD) of amorphous atorvastatin potassium (as prepared in Example 21)

Described herein is an amorphous form of atorvastatin potassium. The amorphous form may be characterized by an X-ray powder diffractogram as depicted in FIG. 22 or 23.

Another aspect of the present invention is a process for preparing amorphous atorvastatin potassium. The method of preparing amorphous atorvastatin potassium comprises grinding atorvastatin potassium Form I in the presence of water.

Preferably, about 1 to about 5 drops of water is used in the above described process. More preferably, about 2 to about 4, or about 2 to about 3, drops of water is used. Preferably, about 1, 2, 3, 4, or 5 drops of water (i.e., about 1, 2, 3, 4, 5, 6, 7, 8, 9, or 10 ml of water) is used per 50 mg of atorvastatin potassium Form I.

The present invention also provides a method for preparing amorphous atorvastatin potassium comprising exposing atorvastatin potassium Form I to about 70% to about 100% relative humidity.

Preferably, the exposure is to about 100% relative humidity

Exposure of atorvastatin potassium Form I to relative humidity is preferably for a period of about 5 to about 14 days, more preferably for about 5 to about 10 days, and most preferably for about 7 days. Preferably, exposure is at a temperature of about 15° C. to about 25° C.

Figure 21:
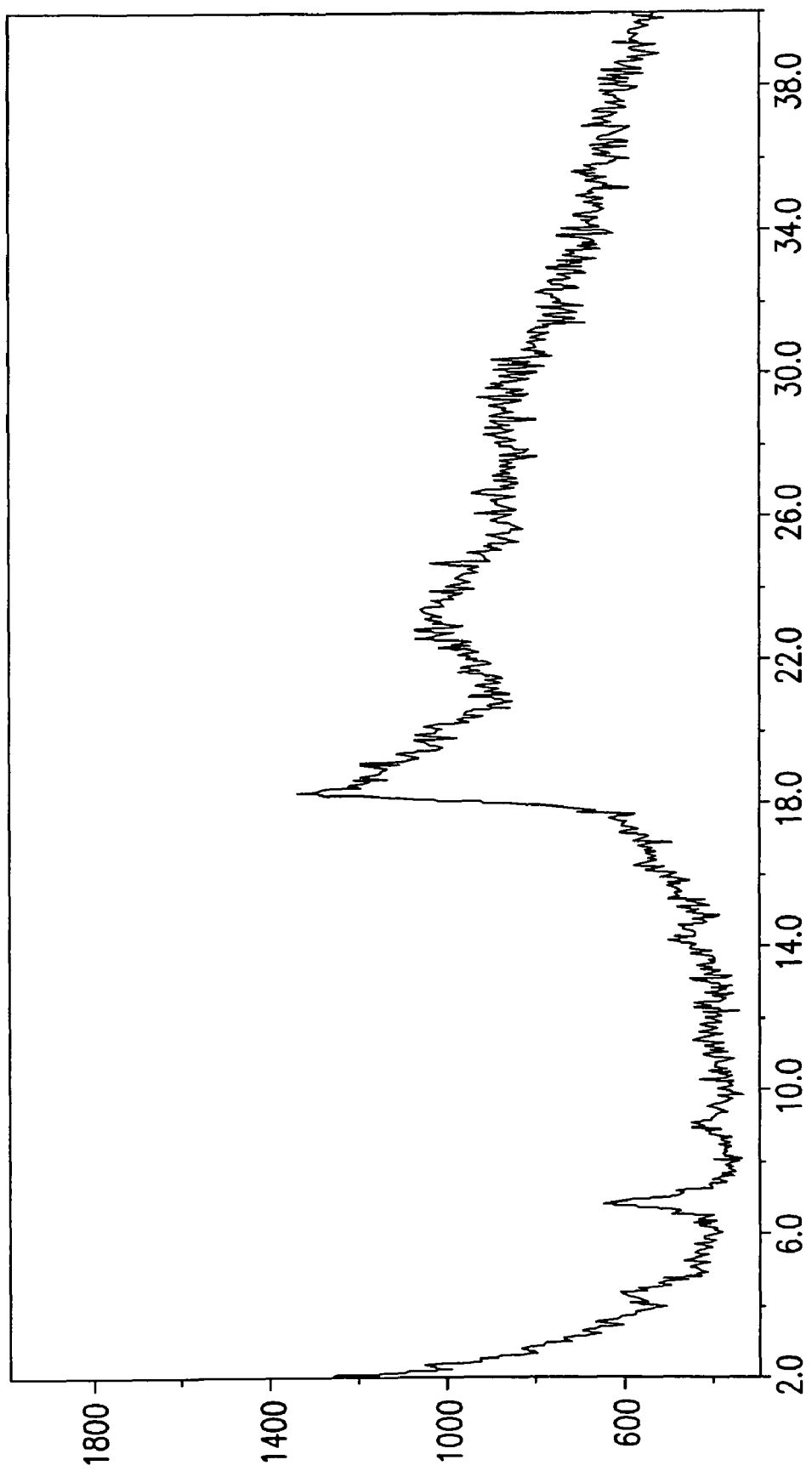
FIG. 21 is a characteristic powder X-ray diffraction pattern (XRPD) of atorvastatin potassium Form G (as prepared in Example 18)

The present invention further encompasses a crystalline form of atorvastatin potassium, denominated as Form G, characterized by an X-ray powder diffraction (XRPD) pattern having two broad peaks with maxima at about 7.1-7.4 and at about 18.4-20.4±0.2 degrees 2θ, as depicted in FIG. 21.

Another aspect of the present invention is a process for preparing atorvastatin potassium Form G. The method of preparing atorvastatin potassium Form G comprises grinding amorphous atorvastatin potassium in the presence of water.

Grinding in any of the processes described above is preferably performed using a mortar and pestle. Preferably, grinding is performed for a period of about 0.5 minute to about 5 minutes, more preferably for about 1 minute to about 3 minutes, and most preferably for about 1 minute. The time frame and equipment used for grinding can be modified for use on an industrial scale.

The present invention further encompasses a process for preparing atorvastatin potassium Form G comprising exposing amorphous atorvastatin potassium to about 70% to about 100% relative humidity.

Preferably, the exposure is to about 100% relative humidity.

Exposure of amorphous atorvastatin potassium to relative humidity is preferably for a period of about 5 to about 14 days, more preferably for about 5 to about 10 days, and most preferably for about 7 days. Preferably, exposure is at a temperature of about 15° C. to about 25° C.

The present invention further encompasses 1) a pharmaceutical composition comprising the atorvastatin potassium crystalline Forms A, B, E, F, or G described above and at least one pharmaceutically acceptable excipient, and 2) the use of the above-described atorvastatin potassium crystalline Forms A, B, E, F, or G for the manufacture of a pharmaceutical composition, wherein the pharmaceutical composition is useful for the treatment of hypercholesterolemia or hyperlipidemia.

The pharmaceutical composition of the present invention can be in a solid or a non-solid form. If the pharmaceutical composition is in a non-solid form, the atorvastatin potassium crystalline Forms A, B, E, F, or G in the composition can be present as a solid in the non-solid pharmaceutical composition, e.g., as a suspension, foam, ointment, etc.

The pharmaceutical composition can be prepared by a process comprising combining the above-described atorvastatin potassium crystalline Forms A, B, E, F, or G with at least one pharmaceutically acceptable excipient. The atorvastatin potassium crystalline Forms A, B, E, F, or G can be obtained by any of the processes of the present invention as described above.

The pharmaceutical composition can be used to make appropriate dosage forms such as tablets, powders, capsules, suppositories, sachets, troches and lozenges.

The atorvastatin potassium crystalline Forms A, B, E, F, or G of the present invention, particularly in a pharmaceutical composition and dosage form, can be used to treat hypercholesterolemia or hyperlipidemia in a mammal such as a human, such treatment comprising administering a treatment effective amount of the atorvastatin potassium crystalline Forms A, B, E, F, or G to the mammal. The treatment effective amount or proper dosage to be used can be determined by one of ordinary skill in the art, and can depend on the method of administration, the bioavailability of the crystalline form, the age, sex, symptoms and health condition of the patient, and the severity of the disease to be treated, etc.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Preferred methods of measuring the experimental parameters described above are set forth below.

XRD

Powder X-ray diffraction ("PXRD") analysis was carried out using a SCINTAG powder X-ray diffractometer model X'TRA equipped with a solid-state detector. Copper radiation of λ=1.5418 angstroms was used. The sample was introduced using a round standard aluminum sample holder with round zero background quartz plate in the bottom. Scanning parameters: scanning range: 2-40 degrees two theta, step: 0.05°, integration time: 1 sec. Scanning with spin.

Solid State NMR

Instrument parameters:
$^{13}$C NMR at 125 MHz using Bruker Avance II+ 500
SB probe using 4 mm rotors
Magic angle was set using KBr
Homogeneity of magnetic field checked using adamantane
Parameters for cross polarization optimized using glycine
Spectral reference set according to glycine as external standard (176.03 ppm for low field carboxyl signal)
Scanning parameters:
Magic Angle Spinning Rate: 11 kHz
Pulse Program: cp with tppm15 during decoupling
Delay time: 2 s
Number of Scans: 2048

TGA Analysis

TGA analysis was preformed using Mettler 3M with Mettler TG 50 thermobalance.

The weight of the samples was about 10 mg; the samples were scanned at a rate of 10° C./min from 25° C. to 200° C. The oven was constantly purged with nitrogen gas at a flow rate of 40 ml/min. Standard alumina crucibles covered by lids with 1 hole were used.

Water Content-KF

Water content was determined by Karl Fisher analysis using Mettler Toledo DL 38 Karl Fisher Titrator.

Potassium hydroxide (KOH), pyrrole acetonide ester (PAE) and atorvastatin lactone used in the examples provided below are commercially available.

The methods set forth above were used in the Examples of the present application.

EXAMPLES

Preparation of Form A

Example 1

Into a jacketed reactor equipped with a mechanical stirrer and a reflux condenser, under atmospheric conditions, were introduced: 72 ml of water, 3.61 ml of hydrochloric acid (32%), 375 ml of ethanol (abs.) and 30 g of PAE. The reaction mixture was heated to 40±5° C. during 1 hour and allowed to react for approximately 7 hours. 150 ml of ethanol (abs.) was added to the reactor and then 150 ml of the mixture was distilled out. The mixture was left to stir overnight. 6.66 g of potassium hydroxide were added to the reactor and the reaction was carried out for 3 hours at 40±5° C. After the reaction had concluded salts were mechanically filtered from the solution. The solution was evaporated using a rotovapor device until a dry white substance was obtained.

Example 2

The same as example 1, except the final drying step. After filtration, the solution was returned to the reactor and concentrated at reflux conditions until half the amount had been evaporated. At this point the mixture was cooled to 40±5° C. and 20 V of MTBE were dripped into the reactor. The mixture was cooled to 7±5° C. and then allowed to precipitate for 3 hours. The solid atorvastatin potassium salt (16.1 g) was then mechanically filtered and dried overnight in a vacuum oven at 65±5° C.

Example 3

Into a jacketed reactor equipped with a mechanical stirrer and a reflux condenser, under atmospheric conditions, were introduced: 72 ml of water, 3.61 ml of HCl (32%), 375 ml of ethanol abs. and 30 g of PAE. The reaction mixture was heated to 40±5° C. during 1 hour and allowed to react for approximately 7 hours. 150 ml of ethanol abs. was added to the reactor and then 150 ml of the mixture was distilled out. The mixture was left to stir overnight. 6.66 g of KOH were added to the reactor and the reaction was carried out for 3 hours at 40±5° C. After the reaction had concluded salts were mechanically filtered from the solution.

The solution was returned to the reactor and concentrated at reflux conditions until half the amount had been evaporated. At this point the mixture was cooled to 40±5° C. and 20 V of Heptane were dripped into the reactor. The mixture was cooled to 5±5° C. and it was allowed to precipitate for 3 hours. The solid atorvastatin (5.9 g) salt was then mechanically filtered and dried overnight in a vacuum oven at 65±5° C. The XRD pattern of the obtained atorvastatin potassium form A is presented in FIG. 2.

Example 4

Into a jacketed reactor equipped with a mechanical stirrer and a reflux condenser, under atmospheric conditions, were introduced: 72 ml of water, 3.61 ml of HCl (32%), 375 ml of ethanol abs. and 30 g of PAE. The reaction mixture was heated to 40±5° C. during 1 hour and allowed to react for approximately 7 hours. 150 ml of ethanol abs. was added to the reactor and then 150 ml of the mixture was distilled out. The mixture was left to stir overnight. 6.06 g of KOH were added to the reactor and the reaction was carried out for 3 hours at 40±5° C. After the reaction had concluded the mixture was concentrated at reflux conditions until half the amount had been evaporated and then salts were mechanically filtered from the solution.

The solution was returned to the reactor and at this point the mixture was cooled to 40±5° C. and 20 V of MTBE were dripped into the reactor. The mixture was cooled to 7±5° C. were it was allowed to precipitate for 3 hours. The solid atorvastatin (16.1 g) salt was then mechanically filtered and dried overnight in a vacuum oven at 65±5° C. to obtain Form A.

Example 5

Into a jacketed reactor equipped with a mechanical stirrer and a reflux condenser, under atmospheric conditions, were introduced: 30 g of PAE, 72 ml of water, 3.61 ml of HCl (32%), and 375 ml of EtOH abs. The reaction mixture was heated to 40±5° C. during 1 hour and allowed to react for approximately 7 hours. 150 ml of EtOH abs. was added to the reactor and then the same amount of the mixture was distilled out. The mixture was left to stir overnight. 5.76 g of KOH were added to the reactor and the reaction was carried out for approximately 3 hours at 40±5° C. After the reaction had concluded, half of the solvent was distilled off and the insoluble salts were filtered from the solution.

The solution was returned to the reactor and at this point the 600 ml of MTBE were added dropwise at 40±5° C. The resulting mixture was cooled to 7±5° C. during 3 hours and then atorvastatin potassium was allowed to precipitate overnight. The solid atorvastatin potassium salt was then filtered and dried overnight in a vacuum oven at 65±5° C.

Example 6

Into a jacketed reactor equipped with a mechanical stirrer and a reflux condenser under atmospheric conditions, were introduced: 30 g of PAE, 72 ml of water, 3.61 ml of HCl (32%), and 375 ml of EtOH abs. The reaction mixture was heated to 40±5° C. during 1 hour and then allowed to react for approximately 7 hours. 150 ml of EtOH abs. was added to the reactor and then the same amount of the mixture was distilled out. The mixture was left to stir overnight. 5.76 g of KOH were added to the reactor and the reaction was carried out for approximately 3 hours at 40±5° C. After the reaction had concluded, half of the solvent was distilled off and 180 ml of MTBE were added dropwise before the insoluble salts were filtered from the solution.

The solution was returned to the reactor and at this point 420 ml of MTBE were added dropwise at 40±5° C. The resulting mixture was cooled to 5±5° C. during 3 hours and atorvastatin potassium was allowed to precipitate. The solid atorvastatin potassium salt was then filtered and dried overnight in a vacuum oven at 65±5° C.

Example 7

Into a 10 liter jacketed reactor equipped with a mechanical stirrer and a reflux condenser under atmospheric conditions, were introduced: 400 g of PAE, 960 ml of water, 48.1 ml of HCl (32%), and 5000 ml of EtOH abs. The reaction mixture was heated to 40±5° C. during 1 hour and allowed to react overnight. 2000 ml of EtOH abs. was added to the reactor and then the same amount of the mixture was distilled out. 80.1 g of KOH were added to the reactor and the reaction was carried out for approximately 3 hours at 40±5° C. After the reaction had concluded, the solvent was distilled off until the mixture was at a volume of 3 liters and the insoluble salts were filtered from the solution.

500 ml of the solution were introduced into a 3 liter jacketed reactor equipped with a mechanical stirrer and a reflux condenser and 1200 ml of MTBE were added dropwise at 25±5° C. The resulting mixture massively precipitated to form solid atorvastatin potassium salt which was filtered immediately and dried overnight in a vacuum oven at 65±5° C.

Example 8

Into a jacketed reactor equipped with a mechanical stirrer and a reflux condenser under atmospheric conditions, were introduced: 120 ml of water, 60 ml of THF, 3.24 g of KOH and 20 g of atorvastatin lactone. The reaction mixture was heated to 45±5° C. and allowed to homogenize for one hour. The mixture was then cooled to 25±5° C. and stirred for 1.5 hours. The solution was evaporated until a dry yellow gel was obtained and was then dried overnight in a vacuum oven at 65±5° C. The XRD pattern of the obtained atorvastatin potassium form A is presented in FIG. 3.

Example 9

Into a jacketed reactor equipped with a mechanical stirrer and a reflux condenser under atmospheric conditions, were introduced: 30 g PAE, 72 ml of water, 3.61 ml of HCl (32%), and 375 ml of EtOH abs. The reaction mixture was heated to 40±5° C. during 1 hour and allowed to react for approximately 7 hours. 150 ml of EtOH abs. was added to the reactor and then the same amount of the mixture was distilled out. The mixture was left to stir overnight. 6.66 g of KOH were added to the reactor and the reaction was carried out for approximately 3 hours at 40±5° C. After the reaction had concluded the mixture was concentrated at reflux conditions until half the amount had been evaporated and then salts were filtered from the solution.

The solution was returned to the reactor and at this point the 600 ml of MTBE were dripped into the reactor at 40±5° C. The mixture was cooled to 15±5° C. where atorvastatin was allowed to precipitate for 3 hours. The solid atorvastatin potassium salt was then filtered and dried overnight in a vacuum oven at 65±5° C. This process yields approximately 86% atorvastatin potassium (26.9 g, assay of 87.4%) in regards to PAE. FIG. 5a presents the XRPD pattern of the product, Form A of atorvastatin potassium.

Dry atorvastatin potassium obtained above was stirred in 450 ml of ethanol abs. at 40±5° C. in the reactor for approximately 45 minutes. Salts from solution were mechanically filtered out and a clear mother liquor was obtained. The solution was returned to the reactor and 600 ml of MTBE were charged by dripping at 40±5° C. The mixture was cooled to 5±5° C. where purified atorvastatin was allowed to precipitate for 3 hours. The solid atorvastatin potassium salt was then filtered, washed with 60 ml of MTBE and dried overnight in a vacuum oven at 65±5° C. (12.3 g obtained). FIG. 5b presents the XRPD pattern of the product, Form A of atorvastatin potassium.

Example 10

Method A

Into a jacketed reactor equipped with a mechanical stirrer and a reflux condenser under atmospheric conditions, were introduced: 1 eq. atorvastatin lactone, 1 eq. of KOH, and a THF:$H_2O$ mixture with a ratio from 10:0.5 v/v to 10:2 v/v. The reaction mixture was introduced at 4±5° C. and stirred for approximately 2-3 hours at this temperature. At this point, the reaction mixture was filtered to remove foreign objects. Afterwards, the reaction mixture was heated to 40±5° C. during 1 hour and allowed to react for an additional half hour. Once the reaction had concluded, 40-70% of the reaction mixture was distilled out by applying vacuum conditions.

At this point, the mixture was cooled to 15±5° C. and 10-20 V of MTBE were added dropwise. The reaction mixture was cooled again to 5±5° C. during 1.5-3 hours, allowing for atorvastatin potassium to precipitate. The solid atorvastatin potassium salt was then filtered and dried overnight in a stirred vacuum reactor or in a static vacuum oven, both at 65±5° C.

Dry atorvastatin potassium was then placed in a static humidity oven at 40±5° C. with 60-80% relative humidity conditions for at least 24 hours. Afterwards, the product was dried again overnight in a stirred vacuum reactor or in a static vacuum oven at 65±5° C. Alternately, atorvastatin potassium can be dried by fluidization with an air or $N_2$ fed fluidized bed drier (FBD) at 65±5° C. applied for 2-6 hours. Lastly, atorvastatin potassium is milled by micronization to the required particle size.

Method B

Into a jacketed reactor equipped with a mechanical stirrer and a reflux condenser under atmospheric conditions, were introduced: 1 eq. (2 kg) atorvastatin lactone, 1 eq. (223.7 g) of KOH, and a THF (20 L):$H_2O$ (3 L) mixture. The reaction mixture was introduced at 4±5° C. and stirred for approximately 2-3 hours at this temperature. At this point, the reaction mixture was filtered to remove foreign objects and a mixture of THF (4 L): $H_2O$ (0.6 L) was added. Afterwards, the reaction mixture was heated to 40±5° C. for a period of 1 hour and allowed to react for an additional half hour. Once the reaction had concluded, 50% of the reaction mixture was distilled out by applying vacuum conditions.

At this point, the mixture was cooled to 15±5° C. and 40 L of MTBE were added dropwise. The reaction mixture was cooled again to 5±5° C. for a period of 3 hours, allowing for atorvastatin potassium to precipitate. At this point, the mixture was heated to 20° C.±5° C. and an additional amount of 78 L MTBE was added. The mixture was cooled to 5±5° C. and the solid atorvastatin potassium salt was then filtered and dried overnight in a stirred vacuum dryer at 65±5° C.

Dry atorvastatin potassium obtained above was then placed in a static humidity oven at 40±5° C. with 80% RH conditions for at least 24 hours. Afterwards, the product was dried again overnight in a stirred vacuum reactor at 65±5° C. Lastly, atorvastatin potassium is milled by micronization to the required particle size.

Preparation of Form B

Example 11

Into a jacketed reactor equipped with a mechanical stirrer and a reflux condenser under atmospheric conditions, were introduced: 72 ml of water, 3.61 ml of HCl (32%), 375 ml of ethanol abs. and 30 g of PAE. The reaction mixture was heated to 40±5° C. during 1 hour and allowed to react for approximately 7 hours. 150 ml of ethanol abs. was added to the reactor and then 150 ml of the mixture was distilled out. The mixture was left to stir overnight. 6.66 g of KOH were added to the reactor and the reaction was carried out for 3 hours at 40±5° C. After the reaction had concluded salts were mechanically filtered from the solution.

The solution was returned to the reactor and 10V of toluene were added while being cooled to 5±3° C. for 48 hr. At this point the mixture was heated to 111±5° C. and EtOH/$H_2O$ was distilled out. 200 ml of toluene were added and the mixture was cooled again to 40±5° C. and then allowed to precipitate for 3 hours. The solid atorvastatin (11.9 g) salt was then mechanically filtered and dried overnight in a vacuum oven at 65±5° C. The XRD pattern of the obtained atorvastatin potassium Form B is presented in FIG. 8.

Preparation of Form III

Example 12

Into a jacketed reactor equipped with a mechanical stirrer and a reflux condenser under atmospheric conditions, were introduced: 200 ml of IPA, 2.07 g of KOH and 20 g of atorvastatin lactone. The reaction mixture was heated to 45±5° C. during 30 minutes and then 80 ml of the solution were distilled out by vacuum. The mixture was cooled to 25±5° C. and allowed to stir overnight, during which precipitation of a white solid had begun while all the IPA evaporated. 150 ml of IPA was added to dislodge the white sediment that formed in the reactor which was mechanically filtered and washed with 80 ml of IPA. The solid atorvastatin was dried overnight in a vacuum oven at 65±5° C. The XRD pattern of the obtained atorvastatin potassium Form III is presented in FIG. 11.

Example 13

12 grams of dry atorvastatin potassium (obtained in Example 5) was suspended in 180 ml of ethanol abs. at 40±5° C. in the reactor for approximately 45 minutes. Salts from the solution were mechanically filtered out and a clear mother liquor was obtained. The solution was evaporated with rotovapor equipment and then solid atorvastatin potassium was dried overnight in a vacuum oven at 65±5° C. The XRD pattern of the obtained atorvastatin potassium Form III is presented in FIG. 12.

Example 14

9 grams of dry atorvastatin potassium (obtained in Example 6) was suspended in 135 ml of ethanol abs. at 40±5° C. in the reactor for approximately 45 minutes. Salts from solution were mechanically filtered out and a clear mother liquor was obtained. The solution was evaporated with rotovapor equipment and then solid atorvastatin potassium was dried overnight in a vacuum oven at 65±5° C. The XRD pattern of the obtained atorvastatin potassium Form III is presented in FIG. 13.

Preparation of Form I

Example 15

60 grams of dry atorvastatin potassium (obtained in Example 7) was suspended in 900 ml of ethanol abs. at 40±5° C. in the reactor for approximately 45 minutes. Salts from the solution were mechanically filtered out and a clear mother liquor was obtained. 1200 ml of MTBE were added dropwise at 40±5° C. The resulting mixture was cooled to 15±5° C., where massive precipitation caused the formation of solid atorvastatin potassium salt which was filtered immediately and dried overnight in a vacuum oven at 65±5° C. or dried overnight in a partial vacuum oven at 65±5° C. or dried using a fluidized bed drier with an ambient air feed for approximately 4 hours.

Preparation of Form E

Example 16

2-3 drops of water were added to about 200 mg of atorvastatin potassium Form A. The sample with the drops of water was ground for about 1 min by using a mortar and pestle. The sample was analyzed by XRD which confirmed Form E content.

Preparation of Form F

Example 17

2-3 drops of ethanol 96% were added to about 200 mg of atorvastatin potassium Form A. The sample with the drops of ethanol was ground for about 1 min by using a mortar and pestle. The sample was analyzed by XRD which confirmed Form F content.

Preparation of Form G

Example 18

About 200 mg of amorphous atorvastatin potassium was exposed to 100% relative humidity for 7 days at room temperature. Then the sample was analyzed by XRD which confirmed that Form G was obtained.

Example 19

To about 100 mg of amorphous atorvastatin potassium, 1-2 drops of water was added. The material was ground with water by using mortar and pestle for about 1 min. The sample was analyzed immediately by XRD, which confirmed Form G content.

Preparation of Amorphous Form

Example 20

A drop of water was added to about 50 mg of atorvastatin potassium Form I that was placed in a mortar. The powder and the water were strongly ground together with a pestle for 1 minute. The wet sample was analyzed by XRD, which confirmed its amorphous content (as described in FIG. 21).

Example 21

About 100 mg of atorvastatin potassium Form I was exposed to 100% relative humidity (RH) for 7 days at room temperature. The sample was analyzed by XRD after the exposure to humidity, which confirmed its amorphous content (as described in FIG. 22).

Preparation of Pharmaceutical Formulation with Atorvastatin Potassium Form A

Example 22

10 mg of atorvastatin potassium Form A was mixed with the following fillers:

55 mg of lactose spray dried, 31.5 mg of microcrystalline cellulose, 3 mg of croscarmellose sodium and with 0.5 mg of magnesium stearate. All those ingredients were pressed to obtain a disk by using a pressure of 2 tons for 1 min. The obtained disk was analyzed by XRD, which confirmed its atorvastatin potassium Form A content.

We claim:

1. A crystalline form of atorvastatin potassium, denominated as Form A, characterized by data selected from the group consisting of:
    an X-ray powder diffraction pattern having peaks at 2.7 and 8.0±0.3 degrees 2θ and a broad peak with a maximum at 18.5±0.3 degrees 2θ,
    a solid-state $^{13}$C NMR spectrum with signals at 126.5, 133.0 and 167.5±0.2 ppm,
    a solid-state $^{13}$C NMR spectrum having chemical shift differences between the signal exhibiting the lowest chemical shift and another signal in the chemical shift range of 100 to 200 ppm of 10.9, 17.4 and 51.9±0.1 ppm wherein the lowest chemical shift in the chemical shift area of 100 to 200 ppm is at 115.6±1 ppm, and
    combinations thereof.

2. The crystalline form of claim 1, characterized by an X-ray powder diffraction pattern having peaks at 2.7 and 8.0±0.3 degrees 2θ and a broad peak with a maximum at 18.5 ±0.3 degrees 2θ.

3. The crystalline form of claim 1, characterized by a solid-state $^{13}$C NMR spectrum with signals at 126.5, 133.0 and 167.5±0.2 ppm.

4. The crystalline form of claim 1, characterized by a solid-state $^{13}$C NMR spectrum having chemical shift differences between the signal exhibiting the lowest chemical shift and another signal in the chemical shift range of 100 to 200 ppm of 10.9, 17.4 and 51.9±0.1 ppm wherein the lowest chemical shift in the chemical shift area of 100 to 200 ppm is at 115.6±1 ppm.

5. The crystalline form of claim 1, characterized by an X-ray powder diffraction pattern as depicted in FIGS. 1-4, 5a or 5b or a solid-state $^{13}$C NMR spectrum as depicted in FIGS. 6 or 7.

6. The crystalline form of claim 1, characterized by having about 4.5% to about 26.4% of water as determined by KF.

7. The crystalline form of claim 1 having less than 5% atorvastatin potassium crystalline Form I and/or Form III.

8. The crystalline form of claim 7 having less than 1% atorvastatin potassium crystalline Form I and/or Form III.

9. A process for preparing atorvastatin potassium Form A comprising mixing atorvastatin, tetrahydrofuran or 2-methyl tetrahydrofuran, water and potassium hydroxide to form a reaction mixture, and precipitating atorvastatin potassium Form A out of the reaction mixture by evaporation.

10. The process of claim 9 wherein evaporation is performed under vacuum.

11. The process of claim 9 wherein an antisolvent that is a liquid $C_4$-$C_6$ ether is added to the evaporated reaction mixture.

12. The process of claim 11 wherein the $C_4$-$C_6$ ether is methyl tert butyl ether.

13. The process of claim 9, wherein the ratio between the tetrahydrofuran or 2-methyl tetrahydrofuran and water is between about 10:0.5 to about 10:2 of tetrahydrofuran or 2-methyl tetrahydrofuran:water (v/v).

14. The process of claim 13, wherein the ratio is about 10:1.5 (v/v).

15. The process of claim 9, wherein the atorvastatin is in its lactone form.

16. The process of claim 15, wherein atorvastatin lactone and potassium hydroxide are added at a ratio of about 1:0.1 to about 1:1 (w/w) of grams atorvastatin lactone to grams potassium hydroxide.

17. The process of claim 16, wherein the ratio is about 1:0.11 (w/w).

18. A pharmaceutical composition comprising atorvastatin potassium crystalline Form A and at least one pharmaceutically acceptable excipient.

19. A process for preparing a pharmaceutical composition comprising atorvastatin potassium crystalline Form A comprising combining atorvastatin potassium crystalline Form A with at least one pharmaceutically acceptable excipient.

* * * * *